US008062893B2

(12) United States Patent
Wang et al.

(10) Patent No.: US 8,062,893 B2
(45) Date of Patent: Nov. 22, 2011

(54) FLUORESCENT SENSOR FOR MERCURY

(75) Inventors: Zidong Wang, Urbana, IL (US); Jung Heon Lee, Evanston, IL (US); Yi Lu, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 168 days.

(21) Appl. No.: 12/564,715

(22) Filed: Sep. 22, 2009

(65) Prior Publication Data

US 2010/0151579 A1    Jun. 17, 2010

Related U.S. Application Data

(60) Provisional application No. 61/104,555, filed on Oct. 10, 2008.

(51) Int. Cl.
G01N 33/20 (2006.01)
G01N 21/64 (2006.01)
(52) U.S. Cl. .................. 436/74; 436/81; 422/82.08
(58) Field of Classification Search .................. 436/74, 436/81; 422/82.08
See application file for complete search history.

(56) References Cited

U.S. PATENT DOCUMENTS

| 4,362,603 A | 12/1982 | Presson et al. |
| 4,703,017 A | 10/1987 | Campbell et al. |
| 4,746,631 A | 5/1988 | Clagett |
| 4,855,240 A | 8/1989 | Rosenstein et al. |
| 4,857,319 A | 8/1989 | Crowe et al. |
| 5,008,109 A | 4/1991 | Tin |
| 5,459,040 A | 10/1995 | Hammock et al. |
| 5,472,881 A | 12/1995 | Beebe et al. |
| 5,580,967 A | 12/1996 | Joyce |
| 5,593,835 A | 1/1997 | Rando et al. |
| 5,631,148 A | 5/1997 | Urdea |
| 5,663,064 A | 9/1997 | Burke et al. |
| 5,807,718 A | 9/1998 | Joyce et al. |
| 5,807,967 A | 9/1998 | Snow et al. |
| 5,910,408 A | 6/1999 | Szostak et al. |
| 5,989,813 A | 11/1999 | Gerdes |
| 6,040,138 A | 3/2000 | Lockhart et al. |

(Continued)

FOREIGN PATENT DOCUMENTS

EP    121970    10/1984

(Continued)

OTHER PUBLICATIONS

Abstract of Joyce, G., "Design and catalytic activity of enzyumic DNA molecules", (1998).

(Continued)

Primary Examiner — Robert J Hill, Jr.
Assistant Examiner — Dwan A Gerido
(74) Attorney, Agent, or Firm — Klarquist Sparkman, LLP

(57) ABSTRACT

The present invention provides a sensor for detecting mercury, comprising: a first polynucleotide, comprising a first region, and a second region, a second polynucleotide, a third polynucleotide, a fluorophore, and a quencher, wherein the third polynucleotide is optionally linked to the second region; the fluorophore is linked to the first polynucleotide and the quencher is linked to the second polynucleotide, or the fluorophore is linked to the second polynucleotide and the quencher is linked to the first polynucleotide; the first region and the second region hybridize to the second polynucleotide; and the second region binds to the third polynucleotide in the presence of $Hg^{2+}$ ions.

27 Claims, 4 Drawing Sheets

U.S. PATENT DOCUMENTS

| | | | |
|---|---|---|---|
| 6,110,462 A | 8/2000 | Barbas et al. |
| 6,159,347 A | 12/2000 | Sumner, Jr. et al. |
| 6,287,765 B1 | 9/2001 | Cubicciotti |
| 6,316,194 B1 | 11/2001 | Karn et al. |
| 6,326,508 B1 | 12/2001 | Godbole et al. |
| 6,361,944 B1 | 3/2002 | Mirkin et al. |
| 6,387,617 B1 | 5/2002 | Asher et al. |
| 6,426,335 B1 | 7/2002 | Janjic et al. |
| 6,451,535 B1 | 9/2002 | Jenne et al. |
| 6,485,982 B1 | 11/2002 | Charlton |
| 6,541,617 B1 | 4/2003 | Bamdad et al. |
| 6,630,306 B1 | 10/2003 | Breaker |
| 6,706,474 B1 | 3/2004 | Lu et al. |
| 6,818,455 B2 | 11/2004 | May et al. |
| 6,843,890 B1 | 1/2005 | Godbole |
| 6,849,414 B2 | 2/2005 | Guan et al. |
| 6,890,719 B2 | 5/2005 | Lu et al. |
| 7,109,165 B2 | 9/2006 | Matulic-Adamic et al. |
| 7,192,708 B2 | 3/2007 | Lu et al. |
| 7,332,283 B2 | 2/2008 | Lu et al. |
| 7,459,145 B2 | 12/2008 | Bao et al. |
| 7,485,419 B2 | 2/2009 | Lu et al. |
| 7,534,560 B2 | 5/2009 | Lu et al. |
| 7,612,185 B2 | 11/2009 | Lu et al. |
| 7,799,554 B2 | 9/2010 | Mazumdar et al. |
| 7,829,350 B2 | 11/2010 | Josephson et al. |
| 7,892,734 B2 | 2/2011 | Lu et al. |
| 7,902,353 B2 | 3/2011 | Lu et al. |
| 7,906,320 B2 | 3/2011 | Lu et al. |
| 2003/0149257 A1* | 8/2003 | Sorge et al. ......... 536/24.3 |
| 2003/0215810 A1 | 11/2003 | Lu et al. |
| 2003/0235611 A1 | 12/2003 | Ehringer et al. |
| 2004/0018515 A1 | 1/2004 | Diener et al. |
| 2004/0110167 A1 | 6/2004 | Gerdes et al. |
| 2004/0126882 A1 | 7/2004 | Ellington et al. |
| 2004/0158051 A1 | 8/2004 | Ozkan et al. |
| 2004/0175693 A1 | 9/2004 | Lu et al. |
| 2005/0037075 A1 | 2/2005 | Farokhzad et al. |
| 2005/0136500 A1 | 6/2005 | Yang et al. |
| 2005/0282186 A1 | 12/2005 | Lu et al. |
| 2006/0019406 A1 | 1/2006 | Wei et al. |
| 2006/0040408 A1 | 2/2006 | Jones et al. |
| 2006/0045910 A1 | 3/2006 | Ehringer |
| 2006/0094026 A1 | 5/2006 | Lu et al. |
| 2006/0166222 A1 | 7/2006 | Lu et al. |
| 2007/0037171 A1 | 2/2007 | Lu et al. |
| 2007/0269821 A1 | 11/2007 | Mazumdar et al. |
| 2008/0176228 A1 | 7/2008 | Lu et al. |
| 2009/0011402 A1 | 1/2009 | Lu et al. |
| 2009/0029874 A1 | 1/2009 | Lu et al. |
| 2009/0197261 A1 | 8/2009 | Lu et al. |
| 2010/0105039 A1 | 4/2010 | Lu et al. |
| 2010/0151579 A1 | 6/2010 | Wang et al. |
| 2010/0166842 A1 | 7/2010 | Lu et al. |
| 2011/0123982 A1 | 5/2011 | Lu et al. |
| 2011/0171635 A1 | 7/2011 | Lu et al. |

FOREIGN PATENT DOCUMENTS

| | | |
|---|---|---|
| EP | 1219708 | 7/2002 |
| EP | 1 312 674 | 5/2003 |
| GB | 2339280 | 1/2000 |
| WO | WO 91/14696 | 10/1991 |
| WO | WO 96/17086 | 6/1996 |
| WO | WO 97/09342 | 3/1997 |
| WO | WO 98/04740 | 2/1998 |
| WO | WO 98/27104 | 6/1998 |
| WO | WO 98/39484 | 9/1998 |
| WO | WO 98/49346 | 11/1998 |
| WO | WO 99/13338 | 3/1999 |
| WO | WO 99/27351 | 6/1999 |
| WO | WO 99/47704 | 9/1999 |
| WO | WO 00/26226 | 5/2000 |
| WO | WO 00/58505 | 10/2000 |
| WO | WO 01/00876 | 1/2001 |
| WO | WO 01/23548 | 4/2001 |
| WO | WO 01/24696 | 4/2001 |
| WO | WO 01/27612 A2 | 4/2001 |
| WO | WO 01/27612 A3 | 4/2001 |
| WO | WO 01/51665 | 7/2001 |
| WO | WO 01/73123 | 10/2001 |
| WO | WO 02/00006 | 1/2002 |
| WO | WO 02/22882 | 3/2002 |
| WO | WO 02/098364 | 12/2002 |
| WO | WO 03/062422 | 7/2003 |
| WO | WO 03/068963 | 8/2003 |
| WO | WO 03/094838 | 11/2003 |
| WO | WO 03/095648 | 11/2003 |
| WO | WO 2004/046687 | 6/2004 |
| WO | WO 2004/081235 | 9/2004 |
| WO | WO 2005/082922 | 9/2005 |
| WO | WO 2005/095967 | 10/2005 |
| WO | WO 2005/100602 | 10/2005 |
| WO | WO 2006/020768 | 2/2006 |
| WO | WO 2006/020786 | 2/2006 |
| WO | WO 2006/048164 | 5/2006 |
| WO | WO 2006/052419 | 5/2006 |
| WO | WO 2006/078660 | 7/2006 |
| WO | WO 2007/106118 | 9/2007 |
| WO | WO 2007/109500 | 9/2007 |
| WO | WO 2008/089248 | 7/2008 |
| WO | WO 2009/012309 | 1/2009 |
| WO | WO 2009/045632 | 4/2009 |

OTHER PUBLICATIONS

Aggarwal, S.K., et al., "Determination of lead in urine and whole blood by stable isotope dilution gas chromatography-mass spectrometry", Clinical Chemistry, vol. 40, No. 8, pp. 1494-1502, (1994).

Alivisatos, A.P., et al., "Organization of "nanocrystal molecules" using DNA", Nature, vol. 382, pp. 609-611, (1996).

Allara, D. et al., "Spontaneously organized molecular assemblies. 1.Formation, dynamics and physical properties of n-alkanoic acids adsorbed from solution on an oxidized aluminum surface", Langmuir, vol. 1, No. 1, pp. 45-52, (1985).

Andreola, M-L., et al., "DNA aptamers selected against the HIV-1 RNase H display in vitro antiviral activity", Biochemistry, vol. 40, No. 34, pp. 10087-10094, (2001).

Bain, C. D., et al., "Modeling organic surfaces with self-assembled monolayers", Angew. Chem. Int. Ed. Engl., vol. 28, No. 4, pp. 506-512, (1989).

Bannon, D.I., et al., "Graphite furnace atomic absorption spectroscopic measurement of blood lead in matrix-matched standards", Clinical Chemistry, vol. 40, No. 9, pp. 1730-1734, (1994).

Been, M.D., et al., "Self-cleaving ribozymes of hepatitis delta virus RNA", Eur. J. Biochem., vol. 247, pp. 741-753, (1997).

Berens, C., et al., "A tetracycline-binding RNA aptamer", Bioorganic & Medicinal Chemistry, vol. 9, pp. 2549-2556, (2001).

Biroccio, A., et al., "Selection of RNA aptamers that are specific and high-affinity ligands of the hepatitis C virus RNA-dependent RNA polymerase", Journal of Virology, vol. 76, No. 8, pp. 3688-3696, (2002).

Blake, D.A., et al., "Antibody-based sensors for heavy metal ions", Biosensors & Bioelectronics, vol. 16, pp. 799-809, (2001).

Blank, M., et al., "Systematic evolution of a DNA aptamer binding to rat brain tumor microvessels. Selective targeting of endothelial regulatory protein pigpen", Journal of Biological Chemistry, vol. 276, No. 19, pp. 16464-16468, (2001).

Bock, L.C., et al., "Selection of single-stranded DNA molecules that bind and inhibit human thrombin", Nature, vol. 355, pp. 564-566, (1992).

Bogden, J.D., et al., "Soil contamination from lead in paint chips", Bulletin of Environmental Contamination & Toxicology, vol. 14, No. 3, pp. 289-294, (1975).

Boiziau, C., et al., "DNA aptamers selected against the HIV-1 transactivation-responsive RNA element form RNA-DNA kissing complexes", Journal of Biological Chemistry, vol. 274, No. 18, pp. 12730-12737, (1999).

Bowins, R.J., et al., "Electrothermal isotope dilution inductively coupled plasma mass spectrometry method for the determination of sub-ng $ml^{-1}$ levels of lead in human plasma", Journal of Analytical Atomic Spectrometry, vol. 9, pp. 1233-1236, (1994).

Breaker, R.R., "Catalytic DNA: in training and seeking employment", Nature Biotechnology, vol. 17, pp. 422-423, (1999).
Breaker, R.R., "DNA aptamers and DNA enzymes" Current Opinion in Chemical Biology, vol. 1, pp. 26-31, (1997).
Breaker, R.R., "DNA enzymes", Nature Biotechnology, vol. 15, pp. 427-431, (1997).
Breaker, R.R., "Molecular Biology: Making Catalytic DNAs", Science, vol. 290, issue 5499, pp. 2095-2096, (2000).
Breaker, R.R., et al., "A DNA enzyme that cleaves RNA", Chemistry & Biology, vol. 1, No. 4, pp. 223-229, (1994).
Breaker, R.R., et al., "A DNA enzyme with $Mg^{2+}$-dependent RNA phosphoesterase activity", Chemistry & Biology, vol. 2, No. 10, pp. 655-660, (1995).
Breaker, R.R., et al., "Engineered allosteric ribozymes as biosensor components", Current Opinion in Biotechnology, vol. 13, pp. 31-39, (2002).
Brody, E.N., et al., "Aptamers as therapeutic and diagnostic agents", Reviews in Molecular Biotechnology, vol. 74, pp. 5-13, (2000).
Broude, N. E., "Stem-loop oligonucleotides: a robust tool for molecular biology and biotechnology", Trends in Biotechnology, vol. 20, No. 6, pp. 249-256, (2002).
Brown, A.K., et al., "A lead-dependent DNAzyme with a two-step mechanism", Biochemistry, vol. 42, No. 23, pp. 7152-7161, (2003).
Bruesehoff, P.J., et al., "Improving metal ion specificity during in Vitro selection of catalytic DNA", Combinatorial Chemistry & High Throughput Screening, vol. 5, pp. 327-335, (2002).
Bruno, J.G., et al., "In vitro selection of DNA aptamers to anthrax spores with electrochemiluminescence detection", Biosensors & Bioelectronics, vol. 14, pp. 457-464, (1999).
Bruno, J.G., et al., "Use of magnetic beads in selection and detection of biotoxin aptamers by electrochemiluminescence and enzymatic methods", BioTechniques, vol. 32, No. 1, pp. 178-180, pp. 182-183, (2002).
Brust, M., et al., "Novel gold-dithiol nano-networks with non-metallic electronic properties", Advanced Materials, vol. 7, No. 9, pp. 795-797, (1995).
Burdette, S.C., et al., "Fluorescent Sensors for $Zn^{2+}$ Based on a Fluorescein Platform: Synthesis, Properties and Intracellular Distribution", J. Am. Chem. Soc., vol. 123, No. 32, pp. 7831-7841, (2001).
Burgstaller, P., et al., "Isolation of RNA aptamers for biological cofactors by in vitro selection", Angew. Chem. Int. Ed. Engl, vol. 33, No. 10, pp. 1084-1087, (1994).
Burgstaller, P., et al., "Structural probing and damage selection of citrulline- and arginine-specific RNA aptamers identify base positions required for binding", Nucleic Acids Research, vol. 23, No. 23, pp. 4769-4776, (1995).
Burke, D.H., et al., "A Novel Acidophilic RNA Motif That Recognizes Coenzyme A", Biochemistry, vol. 37, No. 13, pp. 4653-4663, (1998).
Burke, D.H., et al., "RNA aptamers to the adenosine moiety of S-adenosyl methionine: structural inferences from variations on a theme and the reproducibility of SELEX", Nucleic Acids Research, vol. 25, No. 10, pp. 2020-2024, (1997).
Burke, D.H., et al., "RNA aptamers to the peptidyl transferase inhibitor chloramphenicol", Chemistry & Biology, vol. 4, No. 11, pp. 833-843, (1997).
Burmeister, J., et al., "Cofactor-assisted self-cleavage in DNA libraries with a 3'-5'-phosphoramidate bond", Angew. Chem. Int. Ed. Engl., vol. 36, No. 12, pp. 1321-1324, (1997).
Burwell Jr., R.L., "Modified silica gels as adsorbents and catalysts", Chemical Technology, 4, pp. 370-377, (1974).
Cadwell, R.C., et al., "Mutagenic PCR", PCR Methods and Applications, vol. 3, pp. S136-S140, (1994).
Cadwell, R.C., et al., "Randomization of genes by PCR mutagenesis", PCR Methods and Applications, vol. 2, pp. 28-33, (1992).
Cake, K.M., et al., "In vivo x-ray fluorescence of bone lead in the study of human lead metabolism: serum lead, whole blood lead, bone lead, and cumulative exposure", Advances in X-Ray Analysis, vol. 38, pp. 601-606, (1995).
Camara Rica, C., et al., "Determination of trace concentrations of lead and nickel in human milk by electrothermal atomisation atomic absorption spectrophotometry and inductively coupled plasma emission spectroscopy", The Science of the Total Environment, vol. 22, pp. 193-201, (1982).
Cao, Y.W., et al., "DNA-modified core-shell Ag/Au nanoparticles", J. Am. Chem. Soc., vol. 123, No. 32, pp. 7961-7962, (2001).
Carmi, N., et al., "Cleaving DNA with DNA", Proc. Natl. Acad. Sci. USA, vol. 95, pp. 2233-2237, (1998).
Carmi, N., et al., "In vitro selection of self-cleaving DNAs", Chemistry & Biology, vol. 3, No. 12, pp. 1039-1046, (1996).
Cech, T.R., "Structure and mechanism of the large catalytic RNAs: group I and group II introns and ribonuclease P", The RNA World, pp. 239-269, Cold Spring Harbor Laboratory Press, Cold Spring Harbor, New York, (1993).
Cech, T.R., et al., "Group I ribozymes: substrate recognition, catalytic strategies, and comparative mechanistic analysis", Nucleic Acids and Molecular Biology, vol. 10, pp. 1-17, (1996).
Chaloin, L., et al., "Endogenous expression of a high-affinity pseudoknot RNA aptamer suppresses replication of HIV-1", Nucleic Acids Research, vol. 30, No. 18, pp. 4001-4008, (2002).
Chapman, K.B., et al., "In vitro selection of catalytic RNAs", Current Opinion in Structural Biology, vol. 4, pp. 618-622, (1994).
Chartrand, P., et al., "Effect of structural modifications on the activity of the leadzyme", Biochemistry, vol. 36, no. 11, pp. 3145-3150, (1997).
Chen, J., et al., "Synthesis from DNA of a molecule with the connectivity of a cube", Nature, vol. 350, pp. 631-633, (1991).
Chen, C-T., et al., "A highly selective fluorescent chemosensor for lead ions", J. Am. Chem. Soc., vol. 124, pp. 6246-6247, (2002).
Chen, J-H., et al., "A specific quadrilateral synthesized from DNA branched junctions", J. Am. Chem. Soc., vol. 111, No. 16, pp. 6402-6407, (1989).
Chen, L., et al., "Crystal structure of a four-stranded intercalated DNA: $d(C_4)$", Biochemistry, vol. 33, No. 46, pp. 13540-13546, (1994).
Chinnapen, D.J.F., et al., "Hemin-stimulated docking of cytochrome c to a hemin—DNA aptamer complex", Biochemistry, vol. 41, No. 16, pp. 5202-5212, (2002).
Ciesiolka, J., et al., "Selection of an RNA domain that binds $Zn^{2+}$", RNA, vol. 1, pp. 538-550, (1995).
Ciesiolka, J., et al., "Small RNA-divalent domains", RNA, vol. 2, pp. 785-793, (1996).
Conaty, J., et al., "Selected classes of minimised hammerhead ribozyme have very high cleavage rates at low $Mg^{2+}$ concentration", Nucleic Acids Research, vol. 27, No. 11, pp. 2400-2407, (1999).
Conn, M.M., et al., "Porphyrin Metalation Catalyzed by a Small RNA Molecule", J. Am. Chem. Soc, vol. 118, No. 29, pp. 7012-7013, (1996).
Connell, G.J., et al., "RNAs with dual specificity and dual RNAs with similar specificity", Science, New Series, vol. 264, issue 5162, pp. 1137-1141, (1994).
Connell, G.J., et al., "Three small ribooligonucleotides with specific arginine sites", Biochemistry, vol. 32, No. 21, pp. 5497-5502, (1993).
Cuenoud, B., et al., "A DNA metalloenzyme with DNA ligase activity", Nature, vol. 375, pp. 611-614, (1995).
Czarnik, A.W., "Desperately seeking sensors", Chemistry & Biology, vol. 2, No. 7, pp. 423-428, (1995).
Dai, X., et al., "Cleavage of an amide bond by a ribozyme", Science, New Series, vol. 267, issue 5195, pp. 237-240, (1995).
Davis, J.H., et al., "Isolation of high-affinity GTP aptamers from partially structured RNA libraries", Proc. Natl. Acad. Sci. USA, vol. 99, No. 18, pp. 11616-11621, (2002).
Davis, K.A., et al., "Staining of cell surface human CD4 with 2'-F-pyrimidine-containing RNA aptamers for flow cytometry", Nucleic Acids Research, vol. 26, No. 17, pp. 3915-3924, (1998).
Definition of the word "ion" printed from Merriam-Webster online dictionary (www.m-w.com) on Jun. 30, 2004.
Definition of the word "particle" printed from Merriam-Webster online dictionary (www.m-w.com) on Jun. 29, 2004.
Deo, S., et al., "A Selective, Ratiometric Fluorescent Sensor for $Pb^{2+}$" J. Am. Chem. Soc., vol. 122, No. 1, pp. 174-175, (2000).
Derose, V.J., "Two Decades of RNA Catalysis", Chemistry & Biology, vol. 9, pp. 961-969, (2002).

Didenko, V.V., "DNA probes using fluorescence resonance energy transfer (FRET): Designs and applications", BioTechniques, vol. 31, pp. 1106-1121, (2001). We have reference, but we are missing pp. 1119-1121.
Doudna, J.A., et al., "The Chemical Repertoire of Natural Ribozymes", Nature, vol. 418, pp. 222-228, (2002).
Dubois, L.H., et al., "Synthesis, structure, and properties of model organic surfaces", Annu. Rev. Phys. Chem., vol. 43, pp. 437-463, (1992).
Earnshaw, D.J., et al., "Modified oligoribonucleotides as site-specific probes of RNA structure and function", Biopolymers (Nucleic Acid Sciences), vol. 48, pp. 39-55, (1998).
Ekland, E.H., et al., "RNA-catalysed RNA polymerization using nucleoside triphosphates", Nature, vol. 382, pp. 373-376, (1996).
Ekland, E.H., et al., "Structurally complex and highly active RNA ligases derived from random RNA sequences", Science, vol. 269, issue 5222, pp. 364-370, (1995).
Elghanian, R., et al., "Selective colorimetric detection of polynucleotides based on the distance-dependent optical properties of gold nanoparticles", Science, vol. 277, pp. 1078-1081, (1997).
Ellington, A.D., et al., "Aptamers as potential nucleic acid pharmaceuticals", Biotechnology Annual Review, vol. 1, pp. 185-214, (1995).
Ellington, A.D., et al., "In vitro selection of RNA molecules that bind specific ligands", Nature, vol. 346, pp. 818-822, (1990).
Ellington, A.D., et al., "Selection in vitro of single-stranded DNA molecules that fold into specific ligand-binding structures", Nature, vol. 355, pp. 850-852, (1992).
Famulok, M., "Molecular Recognition of Amino Acids by RNA-Aptamers: An L-Citrulline Binding RNA Motif and Its Evolution into an L-Arginine Binder", J. Am. Chem. Soc., vol. 116, No. 5, pp. 1698-1706, (1994).
Famulok, M., "Oligonucleotide aptamers that recognize small molecules", Current Opinion in Structural Biology, vol. 9, pp. 324-329, (1999).
Famulok, M., et al., "In Vitro Selection Analysis of Neomycin Binding RNAs with a Mutagenized Pool of Variants of the 16S rRNA Decoding Region", Biochemistry, vol. 35, No. 14, pp. 4265-4270, (1996).
Famulok, M., et al., "Stereospecific recognition of tryptophan agarose by in vitro selected RNA", J. Am. Chem. Soc., vol. 114, No. 10, pp. 3990-3991, (1992).
Faulhammer, D., et al., "Characterization and Divalent Metal-ion Dependence of in Vitro Selected Deoxyribozymes which Cleave DNA/RNA Chimeric Oligonucleotides", J. Mol. Biol., vol. 269, pp. 188-202, (1997).
Faulhammer, D., et al., "The $CA^{2+}$ ion as a cofactor for a novel RNA-cleaving deoxyribozyme", Angew. Chem., Int. Ed. Engl., vol. 35, No. 23/24, pp. 2837-2841, (1996).
Feldman, B.J., et al., "Determination of lead in blood by square wave anodic stripping voltammetry at a carbon disk ultramicroelectrode", Analytical Chemistry, vol. 66, No. 13, pp. 1983-1987, (1994).
Ferguson, A., et al., "A novel strategy for selection of allosteric ribozymes yields riboreporter$^{1M}$ sensors for caffeine and aspartame", Nucleic Acids Research, vol. 32, No. 5, pp. 1756-1766, (2004).
Fodor, S.P.A., et al., "Light-directed, spatially addressable parallel chemical synthesis", Science, New Series, vol. 251, issue 4995, pp. 767-773, (1991).
Frank, D.N., et al., "In vitro selection for altered divalent metal specificity in the RNase P RNA", Proc. Natl. Acad. Sci. USA, vol. 94, pp. 14355-14360, (1997).
Frens, G., et al., "Controlled Nucleation for the regulation of the particle size in monodisperse gold suspensions", Nature Physical Science, vol. 241, pp. 20-22, (1973).
Fukusaki, E-l., et al., "DNA aptamers that bind to chitin", Bioorganic & Medicinal Chemistry letters, vol. 10, pp. 423-425, (2000).
Geiger, A., et al., "RNA aptamers that bind L-arginine with sub-micromolar dissociation constants and high enantioselectivity", Nucleic Acids Research, vol. 24, No. 6, pp. 1029-1036, (1996).
Geyer, C.R., et al., "Evidence for the metal-cofactor independence of an RNA phosphodiester-cleaving DNA enzyme", Chemistry & Biology, vol. 4, No. 8, pp. 579-593, (1997).

Geyer, C.R., et al., "Lanthanide Probes for a Phosphodiester-cleaving, Lead-dependent, DNAzyme", J. Mol. Biol., vol. 275, pp. 483-489, (1998).
Giver, L., et al., "Selection and design of high-affinity RNA ligands for HIV-1 Rev", Gene, vol. 137, pp. 19-24, (1993).
Giver, L., et al., "Selective optimization of the Rev-binding element of HIV-1",Nucleic Acids Research, vol. 21, No. 23, pp. 5509-5516, (1993).
Godwin, H.A., et al., "A Flourescent Zinc Probe Based on Metal-Induced Peptide Folding", J. Am. Chem. Soc., vol. 118, pp. 6514-6515, (1996).
Grabar, K., et al., "Preparation and characterization of Au colloid Monolayers", Analytical chemistry, vol. 67, No. 4, pp. 735-743, (1995).
Granadillo, V.A., et al., "The influence of the blood levels of lead, aluminum and vanadium upon the arterial hypertension", Clinica Chimica Acta, vol. 233, pp. 47-59, (1995).
Grate, D., et al., "Laser-mediated, site-specific inactivation of RNA transcripts", Proc. Natl. Acad. Sci. USA, vol. 96, pp. 6131-6136, (1999).
Guschin, D., et al., "Manual manufacturing of oligonucleotide, DNA, and protein microchips", Analytical Biochemistry, vol. 250, pp. 203-211, (1997).
Haller, A.A., et al., "In vitro selection of a 7-methyl-guanosine binding RNA that inhibits translation of capped mRNA molecules", Proc. Natl. Acad. Sci. USA, vol. 94, pp. 8521-8526, (1997).
Harada, K., et al., "Identification of two novel arginine binding DNAs", The EMBO Journal, vol. 14, No. 23, pp. 5798-5811, (1995).
Hartig, J.S., et al., "Reporter ribozymes for real-time analysis of domain-specific interactions in biomolecules: HIV-1 reverse transcriptase and the primer-template complex", Angew. Chem. Int. Ed., vol. 41, No. 22, pp. 4263-4266, (2002).
He, X-x., et al., "Bioconjugated nanoparticles for DNA protection from cleavage", J. Am. Chem. Soc., vol. 125, No. 24, pp. 7168-7169, (2003).
Hennrich, G., et al., "Redox switchable fluorescent probe selective for either Hg(II) or Cd(II) and Zn(II)" J. Am. Chem. Soc., vol. 121, No. 21, pp. 5073-5074, (1999).
Hesselberth, J., et al., "In vitro selection of nucleic acids for diagnostic applications", Reviews in Molecular Biotechnology, vol. 74, pp. 15-25, (2000).
Hesselberth, J.R., et al., "Simultaneous detection of diverse analytes with an aptazyme ligase array", Analytical Biochemistry vol. 312, pp. 106-112, (2003).
Ho, H-A., et al., "Optical sensors based on hybrid aptamer/conjugated polymer complexes", J. Am. Chem. Soc., vol. 126, No. 5, pp. 1384-1387, (2004).
Hock, B., "Antibodies for immunosensors, A review", Analytica Chimica Acta, vol. 347, pp. 177-186, (1997).
Hofmann, H.P., et al., "$Ni^{2+}$-binding RNA motifs with an asymmetric purine-rich internal loop and a G-A base pair", RNA, vol. 3, pp. 1289-1300, (1997).
Holeman, L.A., et al., "Isolation and characterization of fluorophore-binding RNA aptamers", Folding & Design, vol. 3, pp. 423-431, (1998).
Hoogstraten, C.G., et al., "NMR solution structure of the lead-dependent ribozyme: Evidence for dynamics in RNA catalysis", J. Mol. Biol., vol. 284, pp. 337-350, (1998).
Hoogstraten, C.G., et al., "Structural analysis of metal ion ligation to nucleotides and nucleic acids using pulsed EPR spectroscopy", J. Am. Chem. Soc., vol. 124, No. 5, pp. 834-842, (2002).
Huizenga, D.E., et al., "A DNA aptamer that binds adenosine and ATP", Biochemistry, vol. 34, No. 2, pp. 656-665, (1995).
Iler, R.K., "The Chemistry of Silica: Solubility, Polymerization, Colloid and Surface Properties, and Biochemistry, Chapter 6, The surface chemistry of silica", pp. 622-729, A Wiley-Interscience Publication, New York, (1979).
Illangasekare, M., et al., "Small-molecule-substrate interactions with a self-aminoacylating ribozyme", J. Mol. Biol., vol. 268, pp. 631-639, (1997).
Imperiali, B., et al., "Peptide platforms for metal ion sensing", Proc. SPIE—The international society for optical engineering, vol. 3858, pp. 135-143, (1999).

International Search Report dated Jan. 15, 2003 for PCT application No. PCT/US01/20557.

International Search Report dated Aug. 1, 2003 for PCT application No. PCT/US03/08483.

Iqbal, S.S., et al., "A review of molecular recognition technologies for detection of biological threat agents", Biosensors & Bioelectronics, vol. 15, pp. 549-578, (2000).

Abstract of: Iwasaki, K., Mizota, T., Kenkyu Hokoku—Kanagawa-ken Kogyo Shikensho 1991, 62, 57.

Jagner, D., et al., "Determination of lead in microliter amounts of whole blood by stripping potentiometry", Electroanalysis, vol. 6, pp. 285-291, (1994).

Jayasena, S.D., "Aptamers: an emerging class of molecules that rival antibodies in diagnostics", Clinical Chemistry, vol. 45, No. 9, pp. 1628-1650, (1999).

Jenison, R., et al., "Interference-based detection of nucleic acid targets on optically coated silicon", Nature Biotechnology, vol. 19, pp. 62-65, (2001).

Jenison, R.D., et al., "High-resolution molecular discrimination by RNA", Science, vol. 263, pp. 1425-1429, (1994).

Jenne, A., et al., "Rapid Identification and Characterization of Hammerhead-Ribozyme Inhibitors Using Fluorescence-Based Technology", Nature Biotechnology, vol. 19, pp. 56-61, (2001).

Jenne, A., et al., "Real-time Characterization of Ribozymes by Fluorescence Resonance Energy Transfer (FRET)", Angewandte Chemie. International Edition, vol. 38, No. 9, pp. 1300-1303, (1999).

Jhaveri, S., et al., "In vitro selection of signaling aptamers", Nature Biotechnology, vol. 18, pp. 1293-1297, (2000).

Jhaveri, S.D., et al., "Designed signaling aptamers that transduce molecular recognition to changes in fluorescence intensity", J. Am. Chem. Soc., vol. 122, No. 11, pp. 2469-2473, (2000).

Jin, R., et al., "What controls the melting properties of DNA-linked gold nanoparticle assemblies?", J. Am. Chem. Soc., vol. 125, No. 6, pp. 1643-1654, (2003).

Joos, B., et al., "Covalent attachment of hybridizable oligonucleotides to glass supports", Analytical Biochemistry, vol. 247, pp. 96-101, (1997).

Josephson, L., et al., "Magnetic nanosensors for the detection of oligonucleotide sequences", Angewandte Chemie. International Edition, vol. 40, No. 17, pp. 3204-3206, (2001).

Joyce, G.F., "Appendix 3: Reactions Catalyzed by RNA and DNA Enzymes". The RNA World, vol. 37, pp. 687-690, Cold Spring Harbor Laboratory Press, Cold Spring Harbor, New York, (1999).

Joyce, G.F., "In vitro evolution of nucleic acids", Current Opinion in Structural Biology, vol. 4, pp. 331-336, (1994).

Katahira, M., et al., "Two metal-binding sites in a lead ribozyme bound to competitively by $PB^{2+}$ and $Mg^{2+}$: Induced structural changes as revealed by NMR", European Journal of Biochemistry, vol. 255, pp. 727-733, (1998).

Kato, T., et al., "In vitro selection of DNA aptamers which bind to cholic acid", Biochimica et Biophysica Acta, vol. 1493, pp. 12-18, (2000).

Kawakami, J., et al., "In vitro selection of aptamers that act with $Zn^{2+}$", Journal of Inorganic Biochemistry, vol. 82, pp. 197-206, (2000).

Khan, R., et al., "Interaction of retroviral nucleocapsid proteins with transfer $RNA^{Phe}$ : a lead ribozyme and $^1H$ NMR study", Nucleic Acids Research, vol. 24, No. 18, pp. 3568-3575, (1996).

Khosraviani, M., et al., "Detection of heavy metals by immunoassay: Optimization and validation of a rapid, portable assay for ionic cadmium", Environ. Sci. Technol., vol. 32, No. 1, pp. 137-142, (1998).

Kiga, D., et al., "An RNA aptamer to the xanthine/guanine base with a distinctive mode of purine recognition", Nucleic Acids Research, vol. 26, No. 7, pp. 1755-1760, (1998).

Kim, M.H., et al., "Activation and repression of the activity of a lead ribozyme by the combination of $Pb^{2+}$ and $Mg^{2+\ 1}$", J. Biochem., vol. 122, No. 5, pp. 1062-1067, (1997).

Kluβmann, S., et al., "Mirror-image RNA that binds D-adenosine", Nature Biotechnology, vol. 14, pp. 1112-1115, (1996).

Kohama, T., et al., "Molecular Cloning and Functional Characterization of Murine Sphingosine Kinase", The Journal of Biological Chemistry, vol. 273, No. 37, pp. 23722-23728, (1998).

Koizumi, M., et al., "Allosteric selection of ribozymes that respond to the second messengers cGMP and cAMP", Nature Structural Biology, vol. 6, No. 11, pp. 1062-1071, (1999).

Koizumi, M., et al., "Molecular Recognition of cAMP by an RNA Aptamer", Biochemistry, vol. 39, No. 30, pp. 8983-8992, (2000).

Koizumi, M., et al., "Allosteric ribozymes sensitive to the second messengers cAMP and cGMP", Nucleic Acids Symposium Series, No. 42, pp. 275-276, (1999).

Kruger, K., et al., "Self-splicing RNA: autoexcision and autocyclization of the ribosomal RNA intervening sequence of the Tetrahymena", Cell, vol. 31, pp. 147-157, (1982).

Lato, S.M., et al., "In vitro selection of RNA lectins: Using combinatorial chemistry to interpret ribozyme evolution", Chemistry & Biology, vol. 2, No. 5, pp. 291-303, (1995).

Lauhon, C.T., et al., "RNA aptamers that bind flavin and nicotinamide redox cofactors", J. Am. Chem. Soc., vol. 117, No. 4, pp. 1246-1257, (1995).

Lebruska, L.L., "Selection and Characterization of an RNA Decoy for Transcription Factor NF-κB", Biochemistry, vol. 38, No. 10, pp. 3168-3174, (1999).

Lee, M., et al., "A fiber-optic microarray biosensor using aptamers as receptors", Analytical Biochemistry, vol. 282, pp. 142-146, (2000).

Lee, S-W., et al., "Ordering of quantum dots using genetically engineered viruses", Science, vol. 296, pp. 892-895, (2002).

Legault, P., et al., "Order, dynamics and metal-binding in the lead-dependent ribozyme", J. Mol. Biol., vol. 284, pp. 325-335, (1998).

Lehman, N., et al., "Evolution in vitro of an RNA enzyme with altered metal dependence", Nature, vol. 361, pp. 182-185, (1993).

Lemieux, S., et al., "Modeling active RNA structures using the intersection of conformational space: application to the lead-activated ribozyme", RNA, vol. 4, pp. 739-749, (1998).

Levy, M., et al., "ATP-Dependent Allosteric DNA Enzymes", Chemistry & Biology, vol. 9, pp. 417-426, (2002).

Li, J., et al., "A highly sensitive and selective catalytic DNA biosensor for lead ions", J. Am. Chem. Soc., vol. 122, No. 42, pp. 10466-10467, (2000).

Li, J., et al., "In vitro selection and characterization of a highly efficient Zn(II)-dependent RNA-cleaving deoxyribozyme", Nucleic Acids Research, vol. 28, No. 2, pp. 481-488, (2000).

Li, J.J., et al., "Using molecular beacons as a sensitive fluorescence assay for enzymatic cleavage of single-stranded DNA", Nucleic Acids Research, vol. 28, No. 11, e52, pp. i-vi, (2000).

Li, Y., et al., "A catalytic DNA for porphyrin metallation", Nature Structural Biology, vol. 3, No. 9, pp. 743-747, (1996).

Li, Y., et al., "Capping DNA with DNA", Biochemistry, vol. 19, No. 11, pp. 3106-3114, (2000).

Li, Y., et al., "Deoxyribozymes: new players in the ancient game of biocatalysis", Current Opinion in Structural Biology, vol. 9, pp. 315-323, (1999).

Li, Y., et al., "Phosphorylating DNA with DNA", Proc. Natl. Acad. Sci. USA, vol. 96, pp. 2746-2751, (1999).

Link, S., et al., "Alloy formation of gold-silver nanoparticles and the dependence of the plasmon absorption on their composition", J. Phys. Chem. B, vol. 103, No. 18, pp. 3529-3533, (1999).

Liu, H-W., et al., "Determination of cadmium, mercury and lead in seawater by electrothermal vaporization isotope dilution inductively coupled plasma mass spectrometry", Spectrochimica Acta Part B Atomic Spectroscopy 54, pp. 1367-1375, (1999).

Liu, J., et al., "A colorimetric lead biosensor using DNAzyme-directed assembly of gold nanoparticles", J. Am. Chem. Soc., vol. 125, No. 22, pp. 6642-6643, (2003).

Liu, J., et al., "Accelerated color change of gold nanoparticles assembled by DNAzymes for simple and fast colorimetric $Pb^{2+}$ detection", J. Am. Chem. Soc., vol. 126, No. 39, pp. 12298-12305, (2004).

Liu, J., et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J., et al., "Colorimetric biosensors based on DNAzyme-assembled gold nanoparticles", Journal of Fluorescence, vol. 14, No. 4, pp. 343-354, (2004).

Liu, J., et al., "Highly dispersible molecular sieve carbon nanoparticles", Chem. Mater., vol. 16, No. 22, pp. 4205-4207, (2004).

Liu, X., et al., "A fiber-optic evanescent wave DNA biosensor based on novel molecular beacons", Analytical Chemistry, vol. 71, No. 22, pp. 5054-5059, (1999).

Liu, Z., et al., "Assemblage of signaling DNA enzymes with intriguing metal-ion specificities and pH dependences", J. Am. Chem. Soc., vol. 125, No. 25, pp. 7539-7545, (2003).

Lohse, P.A., et al., "Ribozyme-catalysed amino-acid transfer reactions", Nature, vol. 381, pp. 442-444, (1996).

Lorsch, J.R., et al., "In vitro evolution of new ribozymes with polynucleotide kinase activity", Nature, vol. 371, pp. 31-36, (1994).

Lorsch, J.R., et al., "In vitro selection of RNA aptamers specific for cyanocobalamin", Biochemistry, vol. 33, No. 4, pp. 973-982, (1994).

Lott, W.B., et al., "A two-metal ion mechanism operates in the hammerhead ribozyme-mediated cleavage of an RNA substrate", Proc. Natl. Acad. Sci. USA, vol. 95, pp. 542-547, (1998).

Lu, Y., "New transition-metal-dependent DNAzymes as efficient endonucleases and as selective metal biosensors", Chem. Eur. J., vol. 8, No. 20, pp. 4588-4596, (2002).

Lu, Y., et al., "New fluorescent and colorimetric DNAzyme biosensors for metal ions", Journal of Inorganic Biochemistry, vol. 96, issue 1, pp. 30, Abstract of the 11$^{th}$ International Conference on Biological Inorganic Chemistry; (Jul. 15, 2003).

Majerfeld, I., et al., "An RNA pocket for an aliphatic hydrophobe", Structural Biology, vol. 1, No. 5, pp. 287-292, (1994).

Majerfeld, I., et al., "Isoleucine:RNA sites with associated coding sequences", RNA, vol. 4, pp. 471-478, (1998).

Mannironi, C., et al., "In vitro selection of dopamine RNA ligands", Biochemistry, vol. 36, No. 32, pp. 9726-9734, (1997).

Maoz, R., et al., "Penetration-controlled reactions in organized monolayer assemblies. 1. Aqueous permanganate interaction with monolayer and multilayer films of long-chain surfactants", Langmuir, vol. 3, No. 6, pp. 1034-1044, (1987).

Marcus, A.H., et al., "Estimating the contribution of lead based paint to soil lead, dust lead, and childhood blood lead", American Society for Testing and Materials Spec. STP 1226, pp. 12-23, (1995).

Marsh, T.C., et al., "A new DNA nanostructure, the G-wire, imaged by scanning probe microscopy", Nucleic Acids Research, vol. 23, No. 4, pp. 696-700, (1995).

Matteucci, M.D., et al., "Synthesis of Deoxyoligonudeotides on a polymer support", J. Am. Chem. Soc., vol. 103, No. 11, pp. 3185-3191, (1981).

Mecklenburg, M., et al., "A strategy for the broad range detection of compounds with affinity for nucleic acids", Analytica Chimica Acta, vol. 347, pp. 79-86, (1997).

Mei, S.H.J., et al., "An efficient RNA-cleaving DNA enzyme that synchronizes catalysis with fluorescence signaling", J. Am. Chem. Soc., vol. 125, No. 2, pp. 412-420, (2003).

Meli, M., et al., "Adenine-aptamer complexes: A bipartite RNA site that binds the adenine nucleic base", The Journal of Biological Chemistry, vol. 277, No. 3, pp. 2104-2111, (2002).

Mirkin, C.A., et al., "A DNA-based method for rationally assembling nanoparticles into macroscopic materials", Nature, vol. 382, pp. 607-609, (1996).

Mirkin, S.M., et al., "H-DNA and related structures", Annu. Rev. Biophys. Biomol. Struct., vol. 23, pp. 541-576, (1994).

Miyawaki, A., et al. "Fluorescent indicators for $Ca^{2+}$ based on green fluorescent proteins and calmodulin", Nature, vol. 388, pp. 882-887, (1997).

Mucic, R.C., et al., "Synthesis and characterization of DNA with ferrocenyl groups attached to their 5'-termini: electrochemical characterization of a redox-active nucleotide monolayer", Chem. Commun., pp. 555-557, (1996).

Mullah, B., et al., "Automated synthesis of double dye-labeled oligonucleotides using tetramethylrhodamine (TAMRA) solid supports", Tetrahedron Letters, vol. 38, No. 33, pp. 5751-5754, (1997).

Nazarenko, I.A., et al., "A closed tube format for amplification and detection of DNA based on energy transfer", Nucleic Acids Research, vol. 26, No. 12, pp. 2516-2521, (1997).

Nazarenko, I.A., et al., "Defining a Smaller RNA Substrate for Elongation Factor Tu", Biochemistry, vol. 34, No. 8, pp. 2545-2552, (1995).

Niemeyer, C.M., "Nanoparticles, proteins, and nucleic acids: Biotechnology meets materials science", Angew. Chem. Int. Edition, vol. 40, pp. 4128-4158, (2001).

Nieuwlandt, D., et al., "In Vitro Selection of RNA Ligands to Substance P", Biochemistry, vol. 34, No. 16, pp. 5651-5659, (1995).

Nissen, P., et al., "The structural basis of ribosome activity in peptide bond synthesis", Science, vol. 289, pp. 920-930, (2000).

Nolte, A., et al., "Mirror-design of L-oligonucleotide ligands binding to L-arginine", Nature Biotechnology, vol. 14, pp. 1116-1119, (1996).

Nutiu, R., et al., "Structure-switching signaling aptamers", J. Am. Chem. Soc., vol. 125, No. 16, pp. 4771-4778, (2003).

Nuzzo, R.G., et al., "Spontaneously organized molecular assemblies. 3. Preparation and properties of solution adsorbed monolayers of organic disulfides on gold surfaces", J. Am. Chem. Soc., vol. 109, No. 8, pp. 2358-2368, (1987).

O'Donnell, M.J., et al., "High-Density, Covalent Attachment of DNA to Silicon Wafers for Analysis by MALDI-TOF Mass Spectrometry", Analytical Chemistry, vol. 69, No. 13, pp. 2438-2443, (1997).

Oehme, I., et al., "Optical sensors for determination of heavy metal ions", Mikrochim. Acta, vol. 126, pp. 177-192, (1997).

Ohmichi, T., et al., "Role of $Nd^{3+}$ and $Pb^{2+}$ on the RNA cleavage reaction by a small ribozyme", Biochemistry, vol. 36, No. 12, pp. 3514-3521, (1997).

Ohmichi, T., et al., "Effect of substrate RNA sequence on the cleavage reaction by a short ribozyme", Nucleic Acids Research, vol. 26, No. 24, pp. 5655-5661, (1998).

Okazawa, A., et al., "In vitro selection of hematoporphyrin binding DNA aptamers", Bioorganic & Medicinal Chemistry, Letters 10, pp. 2653-2656, (2000).

Ota, N., et al., "Effects of helical structures formed by the binding arms of DNAzymes and their substrates on catalytic activity", Nucleic Acids Research, vol. 26, No. 14, pp. 3385-3391, (1998).

Pan, T., et al., "A small metalloribozyme with a two-step mechanism", Nature, vol. 358, pp. 560-563, (1992).

Pan, T., et al., "In vitro selection of RNAs that undergo autolytic cleavage with $Pb^{2+}$", Biochemistry, vol. 31, No. 16, pp. 3887-3895, (1992).

Pan, T., et al., "Properties of an in vitro selected $Pb^{2+}$ cleavage motif", Biochemistry, vol. 33, No. 32, pp. 9561-9565, (1994).

Pan, W., et al., "Isolation of virus-neutralizing RNAs from a large pool of random sequences", Proc. Natl. Acad. Sci. USA, vol. 92, pp. 11509-11513, (1995).

Park, S.-J., et al., "Array-based electrical detection of DNA with nanoparticle probes", Science, vol. 295, pp. 1503-1506, (2002).

Parsons, P.J., et al., "A rapid Zeeman graphite furnace atomic absorption spectrometric method for the determination of lead in blood", Spectrochimica Acta, vol. 48B, No. 6/7, pp. 925-939, (1993).

Pavlov, A.R., et al., "Determination of lead in environmental water samples by a rapid and portable immunoassay", ANYL, Book of Abstracts, 219th ACS National Meeting, San Francisco, CA, Mar. 26-30, 2000.

Pavlov, V., et al., "Aptamer-functionalized Au nanoparticles for the amplified optical detection of thrombin", J. Am. Chem. Soc., vol. 126, No. 38, pp. 11768-11769, (2004).

Pearce, D.A., et al., "Peptidyl chemosensors incorporating a FRET mechanism for detection of Ni(II)", Bioorganic & Medicinal Chemistry, Letters 8, pp. 1963-1968, (1998).

Pease, A.C., et al., "Light-generated oligonucleotide arrays for rapid DNA sequence analysis", Proc. Natl. Acad. Sci. USA, vol. 91, pp. 5022-5026, (1994).

Piccirilli, J.A., et al., "Aminoacyl esterase activity of the tetrahymena ribozyme", Science, New Series, vol. 256, issue 5062, pp. 1420-1424, (1992).

Pley, H.W., et al., "Three-dimensional structure of a hammerhead ribozyme", Nature, vol. 372, pp. 68-74, (1994).

Potyrailo, R.A., et al., "Adapting selected nucleic acid ligands (aptamers) to biosensors", Analytical Chemistry, vol. 70, No. 16, pp. 3419-3425, (1998).

Prudent, J.R., et al., "Expanding the scope of RNA catalysis", Science, New Series, vol. 264, issue 5167, pp. 1924-1927, (1994).

Qiao, H., et al., "Transferability of blood lead determinations by furnace atomic absorption spectrophotometry and continuum background correction", Clinical Chemistry, vol. 41, No. 10, pp. 1451-1454, (1995).

Rabinowitz, M., et al., "Home refinishing, lead paint, and infant blood lead levels", American Journal of Public Health, vol. 75, No. 4, pp. 403-404, (1985).

Rajendran, M., et al., "Selecting nucleic acids for biosensor applications", Combinatorial Chemistry and High Throughput Screening, vol. 5, No. 4, pp. 263-270, (2002).

Rakow, N.A., et al., "A colorimetric sensor array for odour visualization", Nature, vol. 406, pp. 710-713, (2000).

Rink, S.M., et al., "Creation of RNA molecules that recognize the oxidative lesion 7,8-dihydro-8-hydroxy-2'-deoxyguanosine (8-oxodG) in DNA", Proc. Natl. Acad. Sci. USA, vol. 95, pp. 11619-11624, (1998).

"Design and optimization of effector-activated ribozyme ligases", Nucleic Acids Research, vol. 28, No. 8, pp. 1751-1759, (2000).

Robertson, M.P., et al., "In vitro selection of an allosteric ribozyme that transduces analytes to amplicons", Nature Biotechnology, vol. 17, pp. 62-66, (1999).

Roth, A., et al., "An amino acid as a cofactor for a catalytic polynucleotide", Proc. Natl. Acad. Sci. USA, vol. 95, pp. 6027-6031, (1998).

Roychowdhury-Saha, M., et al., "Flavin Recognition by an RNA Aptamer Targeted toward FAD", Biochemistry, vol. 41, No. 8, pp. 2492-2499, (2002).

Ruckman, J., et al., "2'-Fluoropyrimidine RNA-based aptamers to the 165-amino acid form of vascular endothelial growth factor ($VEGF_{165}$) Inhibition of receptor binding and VEGF-induced vascular permeability through interactions requiring the exon 7-encoded domain", The Journal of Biological Chemistry, vol. 273, No. 32, pp. 20556-20567, (1998).

Rurack, K., et al., "A selective and sensitive fluoroionophore for $Hg^{II}$, $Ag^{I}$, and $Cu^{II}$ with virtually decoupled fluorophore and receptor units", J. Am. Chem. Soc., vol. 122, No. 5, pp. 968-969, (2000).

Rusconi, C.P., et al., "RNA aptamers as reversible antagonists of coagulation factor Ixa", Nature, vol. 419, pp. 90-94, (2002).

Sabanayagam, C.R., et al., "Oligonucleotide immobilization on micropatterened streptavidin surfaces", Nucleic Acids Research, vol. 28, No. 8, e33, pp. i-iv, (2000).

Santoro, S.W. et al., "Mechanism and utility of an RNA-cleaving DNA enzyme", Biochemistry, vol. 37, No. 38, pp. 13330-13342, (1998).

Santoro, S.W., et al., "A general purpose RNA-cleaving DNA enzyme", Proc. Natl. Acad. Sci. USA, vol. 94, pp. 4262-4266, (1997).

Santoro, S.W., et al., "RNA Cleavage by a DNA Enzyme with Extended Chemical Functionality", J. Am. Chem. Soc., vol. 122, No. 11, pp. 2433-2439, (2000).

Sassanfar, M., et al., "An RNA motif that binds ATP", Nature, vol. 364, pp. 550-553, (1993).

Schwartz, J., et al., "The risk of lead toxicity in homes with lead paint hazard", Environmental Research, vol. 54, No. 1, pp. 1-7, (1991).

Scott, W.G., et al., "The crystal structure of an all-RNA hammerhead ribozyme: A proposed mechanism for RNA catalytic cleavage", Cell, vol. 81, pp. 991-1002, (1995).

Scott, W.G., "RNA catalysis", Current Opinion in Structural Biology, vol. 8, pp. 720-726, (1998).

Search results of key word search of medline, Mar. 26, 2000.

Search results of key word search on Chemical Abstracts, Mar. 24, 2000.

Search results of key word search from various databases, Mar. 24, 2000.

Seeman, N.C., et al., "Synthetic DNA knots and catenanes", New Journal of Chemistry, vol. 17, pp. 739-755, (1993).

Seeman, N.C., et al., "Emulating biology: Building nanostructures from the bottom up", Proc. Natl. Acad. Sci., vol. 99, suppl. 2, pp. 6451-6455, (2002).

Seeman, N.C., "DNA in a material world", Nature, vol. 421, pp. 427-431, (2003).

Seetharaman, S., et al., "Immobilized RNA switches for the analysis of complex chemical and biological mixtures", Nature Biotechnology, vol. 19, pp. 336-341, (2001).

Sen, D., et al., "DNA enzymes", Current Opinion in Chemical Biology, vol. 2, pp. 680-687, (1998).

Shaiu, W-L., et al., "Atomic force microscopy of oriented linear DNA molecules labeled with 5nm gold spheres", Nucleic Acids Research, vol. 21, No. 1, pp. 99-103, (1993).

Shaw, S.Y., et al., "Knotting of a DNA chain during ring closure", Science, New Series, vol. 260, issue 5107, pp. 533-536, (1993).

Shekhtman, E.M., et al., "Stereostructure of replicative DNA catenanes from eukaryotic cells", New Journal of Chemistry, vol. 17, pp. 757-763, (1993).

Sigurdsson, S.T., et al., "Small ribozymes", RNA Structure and Function, Cold Spring Harbor Laboratory Press (Monograph 35), pp. 339-375, (1998).

Singh, K.K., et al., "Fluorescence Polarization for Monitoring Ribozyme Reactions in Real-Time", Biotechniques, vol. 29, No. 2, pp. 344-351, (2000).

Smith, F.W., et al., "Quadruplex structure of oxytricha telomeric DNA oligonucleotides", Nature, vol. 356, pp. 164-168, (1992).

Smith, J.O., et al., "Molecular recognition of PNA-containing hybrids: Spontaneous assembly of helical cyanine dye aggregates on PNA templates", J. Am. Chem. Soc., vol. 121, No. 12, pp. 2686-2695, (1999).

Soriaga, M.P., et al., "Determination of the orientation of aromatic molecules adsorbed on platinum electrodes: The effect of solute concentration", J. Am. Chem. Soc., vol. 104, No. 14, pp. 3937-3945, (1982).

Soukup, G.A., et al., "Engineering precision RNA molecular switches", Proc. Natl. Acad. Sci. USA, vol. 96, pp. 3584-3589, (1999).

Soukup, G.A., et al., "Allosteric nucleic acid catalysts", Current Opinion in Structural Biology, vol. 10, pp. 318-325, (2000).

Srisawat, C., et al., "Sephadex-binding RNA ligands: rapid affinity purification of RNA from complex RNA mixtures", Nucleic Acids Research, vol. 29, No. 2 e4, pp. 1-5, (2001).

Stage-Zimmermann, T.K., et al., "Hammerhead ribozyme kinetics", RNA, vol. 4, pp. 875-889, (1998).

Stojanovic, M.N., et al., "Aptamer-based colorimetric probe for cocaine", J. Am. Chem. Soc., vol. 124, No. 33, pp. 9678-9679, (2002).

Stojanovic, M.N., et al., "Aptamer-based folding fluorescent sensor for cocaine", Journal of the American Chemical Society, vol. 123, No. 21, pp. 4928-4931, (2001).

Stojanovic, M.N., et al., "Fluorescent sensors based on aptamer self-assembly", Journal of the American Chemical Society, vol. 122, No. 46, pp. 11547-11548, (2000).

Storhoff, J.J., et al., "Programmed materials synthesis with DNA", Chem. Rev., vol. 99, No. 7, pp. 1849-1862, (1999).

Storhoff, J.J., et al., "Facile colorimetric detection of polynucleotides based on gold nanoparticle probes", Proceedings of the 1998 ERDEC Scientific Conference on Chemical and Biological Defense Research, Nov. 17-20, 1998, Aberdeen Proving Ground, pp. 221-226, (1999).

Storhoff, J.J., et al., "What Controls the Optical Properties of DNA-Linked Gold Nanoparticle Assemblies?", J. Am. Chem. Soc., vol. 122, No. 19, pp. 4640-4650, (2000).

Storhoff, J.J., et al., "One-pot colorimetric differentiation of polynucleotides with single base imperfections using gold nanoparticle probes", Journal of the American Chemical Society, vol. 120, No. 9, pp. 1959-1964, (1998).

Streicher, B., et al., "Lead cleavage site in the core structure of group I intron-RNA", Nucleic Acids Research, vol. 21, No. 2, pp. 311-317, (1993).

Sugimoto, N., et al., "Site-specific cleavage reaction catalyzed by leadzyme is enhanced by combined effect of lead and rare earth ions", FEBS Letters, vol. 393, pp. 97-100, (1996).

Sun, L.Q., et al., "Catalytic nucleic acids: From lab to applications", Pharmacological Reviews, vol. 52, pp. 325-347, (2000).

Tahan, J.E., et al., "Electrothermal atomic absorption spectrometric determination of Al, Cu, Ge, Pb, V and Zn in clinical samples and in certified environmental reference materials", Analytica Chimica Acta, vol. 295, pp. 187-197, (1994).

Takagi, Y., et al., "Survey and Summary: Recent advances in the elucidation of the mechanisms of action of ribozymes", Nucleic Acids Research, vol. 29, No. 9, pp. 1815-1834, (2001).

Tang, J., et al., "Rational design of allosteric ribozymes", Chemistry & Biology, vol. 4, No. 6, pp. 453-459, (1997).

Tang, J., et al., "Structural diversity of self-cleaving ribozymes", Proc. Natl. Acad. Sci. USA, vol. 97, No. 11, pp. 5784-5789, (2000).

Tanner, N. K., "Biochemistry of hepatitis delta virus catalytic RNAs", Ribozymes in the Gene Therapy of Cancer, Chapter 3, pp. 23-38, (1998).

Tao, J., et al., "Arginine-Binding RNAs Resembling TAR Identified by in Vitro Selection", Biochemistry, vol. 35, No. 7, pp. 2229-2238, (1996).

Tarasow, T.M., et al., "RNA-catalysed carbon-carbon bond formation", Nature, vol. 389, pp. 54-57, (1997).

Telting-Diaz, M., et al., "Mass-produced ionophore-based fluorescent microspheres for trace level determination of lead ions", Analytical Chemistry, vol. 74, No. 20, pp. 5251-5256, (2002).

Thompson, R.B., et al., "Determination of Picomolar Concentrations of Metal Ions Using Fluorescence Anisotropy: Biosensing with a "Reagentless" Enzyme Transducer", Analytical Chemistry, vol. 70, No. 22, pp. 4717-4723, (1998).

Timmons, C.O., et al., "Investigation of Fatty Acid Monolayers on Metals by Contact Potential Measurements", Journal of Physical Chemistry, vol. 69, No. 3, pp. 984-990, (1965).

Tompkins, H.G., et al., "The study of the gas-solid interaction of acetic acid with a cuprous oxide surface using reflection-absorption spectroscopy", Journal of Colloid and Interface Science, vol. 49, No. 3, pp. 410-421, (1974).

Travascio, P., et al., "A ribozyme and a catalytic DNA with peroxidase activity: active sites versus cofactor-binding sites", Chemistry & Biology, vol. 6, No. 11, pp. 779-787, (1999).

Tsang, J., et al., "In vitro evolution of randomized ribozymes", Methods in Enzymology, vol. 267, pp. 410-426, (1996).

Tsien, R.Y., "Fluorescent and photochemical probes of dynamic biochemical signals inside living cells", Fluorescent Chemosensors for Ion and Molecule Recognition, (ed. Czarnik, A.W.), chapter 9, pp. 130-146, American Chemical Society, (1993).

Tuerk, C., et al., "RNA pseudoknots that inhibit human immunodeficiency virus type 1 reverse transcriptase", Proc. Natl. Acad. Sci. USA, vol. 89, pp. 6988-6992, (1992).

Tuerk, C., et al., "Systematic evolution of ligands by exponential enrichment: RNA ligands to bacteriophage T4 DNA polymerase", Science, New Series, vol. 249, issue 4968, pp. 505-510, (1990).

Tyagi, S., et al., "Molecular Beacons: Probes that fluoresce upon hybridization", Nature Biotechnology, vol. 14, pp. 303-308, (1996).

Tyagi, S., et al., "Multicolor molecular beacons for allele discrimination", Nature Biotechnology, vol. 16, pp. 49-53, (1998).

Tyagi, S., et al., "Wavelength-shifting molecular beacons", Nature Biotechnology, vol. 18, pp. 1191-1196, (2000).

Ueyama, H., "A novel potassium sensing in aqueous media with a synthetic oligonucleotide derivative. Fluorescence resonance energy transfer associated with guanine quartet-potassium ion complex formation", J. Am. Chem. Soc., vol. 124, No. 48, pp. 14286-14287, (2002).

Uphoff, K.W., et al., "In vitro selection of aptamers: the dearth of pure reason", Current Opinion in Structural Biology, vol. 6, pp. 281-288, (1996).

Vaish, N.K., et al., "In vitro selection of a purine nucleotide-specific hammerhead-like ribozyme", Proc. Natl. Acad. Sci. USA, vol. 95, pp. 2158-2162, (1998).

Valadkhan, S., et al., "Splicing-related catalysis by protein-free snRNAs", Nature, vol. 413, pp. 701-707, (2001).

Vianini, E., et al., "In vitro selection of DNA aptamers that bind L-tyrosinamide", Bioorganic & Medicinal Chemistry, vol. 9, pp. 2543-2548, (2001).

Walkup, G.K., et al., "Design and Evaluation of a Peptidyl Fluorescent Chemosensor for Divalent Zinc", J. Am. Chem. Soc., vol. 118, No. 12, pp. 3053-3054, (1996).

Wallace, S.T., et al., In vitro selection and characterization of streptomycin-binding RNAs: recognition discrimination between antibiotics. RNA, vol. 4, pp. 112-123, (1998).

Wallis, M.G., et al., "A novel RNA motif for neomycin recognition", Chemistry & Biology, vol. 2, No. 8, pp. 543-552, (1995).

Wallis, M.G., et al., "In vitro selection of a viomycin-binding RNA pseudoknot", Chemistry & Biology, vol. 4, No. 5, pp. 357-366, (1997).

Walter, F., et al., "Folding of the four-way RNA junction of the hairpin ribozyme", Biochemistry, vol. 37, No. 50, pp. 17629-17636, (1998).

Walter, N.G., et al., "The hairpin ribozyme: structure, assembly and catalysis", Current Opinion in Chemical Biology, vol. 2, pp. 24-30, (1998).

Wang, D.Y., et al., "A general strategy for effector-mediated control of RNA-cleaving ribozymes and DNA enzymes", J. Mol. Biol., vol. 318, pp. 33-43, (2002).

Wang, F., et al., "Sphingosine-1-phosphate Inhibits Motility of Human Breast Cancer Cells Independently of Cell Surface Receptors", Cancer Research, vol. 59, pp. 6185-6191, (1999).

Wang, J., "Survey and Summary: From DNA biosensors to gene chips", Nucleic Acids Research, vol. 28, No. 16, pp. 3011-3016, (2000).

Wang, K.Y., et al., "A DNA aptamer which binds to and inhibits thrombin exhibits a new structural motif for DNA", Biochemistry, vol. 32, No. 8, pp. 1899-1904, (1993).

Wang, Y., et al., "Assembly and characterization of five-arm and six-arm DNA branched junctions", Biochemistry, vol. 30, pp. 5667-5674, (1991).

Wang, Y., et al., "RNA molecules that specifically and stoichiometrically bind aminoglycoside antibiotics with high affinities", Biochemistry, vol. 35, No. 38, pp. 12338-12346, (1996).

Wecker, M., et al., "In vitro selection of a novel catalytic RNA: characterization of a sulfur alkylation reaction and interaction with a small peptide", RNA, vol. 2, pp. 982-994, (1996).

Wedekind, J.E., et al., "Crystal structure of a lead-dependent ribozyme revealing metal binding sites relevant to catalysis", Nature Structural Biology, vol. 6, No. 3, pp. 261-268, (1999).

Wedekind, J.E., et al., "Crystal structure of the leadzyme at 1.8 Å Resolution: Metal ion binding and the implications for catalytic mechanism and allo site ion regulation", Biochemistry, vol. 42, No. 32, pp. 9554-9563, (2003).

Wells, R.D., "Unusual DNA structures", Journal of Biological Chemistry, vol. 263, No. 3, pp. 1095-1098, (1988).

Werstuck, G., et al., "Controlling gene expression in living cells through small molecule-RNA interactions", Science, vol. 282, pp. 296-298, (1998).

Whaley, S.R., et al., "Selection of peptides with semiconductor binding specificity for directed nanocrystal assembly", Nature, vol. 405, pp. 665-668, (2000).

Whitesides, G.M., et al., "Self-assembled monolayers and lithography", Proceedings of the Robert A. Welch Foundation 39th Conference on Chemical Research on Nanophase Chemistry, pp. 109-121, Houston, TX, Oct. 23-24, 1995.

Wiegand, T.W., et al., "High-affinity oligonucleotide ligands to human IgE inhibit binding to Fc epsilon receptor I", The Journal of Immunology, vol. 157, pp. 221-230, (1996).

Wiegand, T.W., et al., "Selection of RNA amide synthases", Chemistry & Biology, vol. 4, No. 9, pp. 675-683, (1997).

Williams, K.P., et al., "Bioactive and nuclease-resistant L-DNA ligand of vasopressin", Proc. Natl. Acad. Sci. USA, vol. 94, pp. 11285-11290, (1997).

Williams, K.P., et al., "Selection of novel $Mg^{2+}$-dependent self-cleaving ribozymes" The EMBO Journal, vol. 14, No. 18, pp. 4551-4557, (1995).

Wilson, C., et al., "Functional requirements for specific ligand recognition by a biotin-binding RNA Pseudoknot", Biochemistry, vol. 37, No. 41, pp. 14410-14419, (1998).

Wilson, C., et al., "In vitro evolution of a self-alkylating ribozyme", Nature, vol. 374, pp. 777-782, (1995).

Wilson, C., et al., "Isolation of a fluorophore-specific DNA aptamer with weak redox activity", Chemistry & Biology, vol. 5, No. 11, pp. 609-617, (1998).

Wilson, D.S., et al., "In vitro selection of functional nucleic acids", Annu. Rev. Biochem. vol. 68, pp. 611-647, (1999).
Winkler, J.D., et al., "Photodynamic Fluorescent Metal Ion Sensors with Parts per Billion Sensitivity", J. Am. Chem. Soc., vol. 120, No. 13, pp. 3237-3242, (1998).
Wittmann, C., et al.,"Microbial and Enzyme sensors for environmental monitoring", Handbook of Biosensors and Electronic Noses: Medicine, Food, and the Environment, pp. 299-332, (1997).
Xia, P., et al., "Activation of Sphingosine Kinase by Tumor Necrosis Factor-α Inhibits Apoptosis in Human Endothelial Cells", Journal of Biological Chemistry, vol. 274, No. 48, pp. 34499-34505, (1999).
Yan, H., et al., "DNA—Templated self-assembly of protein arrays and highly conductive nanowires", Science, vol. 301, pp. 1882-1884, (2003).
Yang, Q., et al., "DNA ligands that bind tightly and selectively to cellobiose", Proc. Natl. Acad. Sci. USA, vol. 95, pp. 5462-5467, (1998).
English Translation of Yang, Y., et al., "Measurement of lead and magnesium in distilled spirits using inductively coupled plasma optical emission spectrometry viewed from the end", Analytical Chemistry (Fenxi Huaxue), Chinese Journal of Analytical Chemistry, vol. 25, No. 9, pp. 1114-1117, (1997).
Yurke, B., et al., "A DNA-fuelled molecular machine made of DNA", Nature, vol. 406, pp. 605-608, (2000).
Zhang, B., et al., "Peptide bond formation by in vitro selected ribozymes", Nature, vol. 390, pp. 96-100, (1997).
Zhang, P., et al., "Design of a molecular beacon DNA probe with two fluorophores", Angewandte Chemie International Edition, vol. 40, No. 2, pp. 402-405, (2001).
Zillmann, M., et al., "In vitro optimization of truncated stem-loop II variants of the hammerhead ribozyme for cleavage in low concentrations of magnesium under non-turnover conditions", RNA, vol. 3, pp. 734-747, (1997).
Zimmerman, J.M., et al., "In vivo selection of spectinomycin-binding RNAs", Nucleic Acids Research, vol. 30, No. 24, pp. 5425-5435, (2002).
Zimmermann, G.R., et al., "Molecular interactions and metal binding in the theophylline-binding core of an RNA aptamer", RNA, vol. 6, pp. 659-667, (2000).
International Search Report dated Nov. 21, 2005 for PCT application No. PCT/US2005/001060.
Supplemental International Search Report dated Jan. 10, 2006 for PCT application No. PCT/US2005/001060.
Liu, J., et al., "Size control, metal substitution, and catalytic application of cryptomelane nanomaterials prepared using cross-linking reagents", Chem. Mater., vol. 16, No. 2, pp. 276-285, (2004).
Cake, K.M., et al., "Partition of circulating lead between serum and red cells is different for internal and external sources of lead", American Journal of Industrial Medicine, vol. 29, pp. 440-445, (1996).
International Search Report dated Aug. 31, 2004 for PCT application No. PCT/US2004/002946.
Hazarika, P., et al., "Reversible switching of DNA-Gold nanoparticle aggregation", Angewandte Chemie International Edition, vol. 43, No. 47, pp. 6469-6471, (2004).
International Search Report dated May 29, 2006 for PCT application No. PCT/US2005/037896.
Liu, J., et al., "Improving fluorescent DNAzyme biosensors by combining Inter- and Intramolecular quenchers", Analytical Chemistry, vol. 75, No. 23, pp. 6666-6672, (2003).
Liu, J., et al., "Stimuli-responsive disassembly of nanoparticle aggregates for light-up colorimetric sensing", Journal of the American Chemical Society, vol. 127, No. 36, pp. 12677-12683, (2005).
European Search Report dated Jul. 10, 2006 for PCT application No. PCT/US2003/12576.
Tanner, F.C., et al., "Transfection of human endothelial cells", Cardiovascular research, vol. 35, pp. 522-528, (1997).
International Search Report dated Nov. 17, 2006 for PCT application No. PCT/US2006/001627.
Liu, J., et al., "DNAzyme-directed assembly of gold nanoparticles as colorimetric sensor for a broad range of analytes", pp. 1-3, located at http://ieeenano2003.arc.nasa.gov/THM@.pdf, (2003).
Wang, D.Y., et al., "A general approach for the use of oligonucleotide effectors to regulate the catalysis of RNA-cleaving ribozymes and DNAzymes", Nucleic Acids Research, vol. 30, No. 8, pp. 1735-1742, (2002).
Levy, M., et al., "Exponential growth by cross-catalytic cleavage of deoxyribozymogens",PNAS, vol. 100, No. 11, pp. 6416-6421, (2003).
Beyer, S., et al., "A modular DNA signal translator for the controlled release of a protein by an aptamer", Nucleic Acids Research, vol. 34, No. 5, pp. 1581-1587, (2006).
Frauendorf, C., et al., "Detection of small organic analytes by fluorescing molecular switches", Bioorganic & Medicinal Chemistry, vol. 9, pp. 2521-2524, (2001).
Glynou, K., et al., "Oligonucleotide-functionalized gold nanoparticles as probes in a dry-reagent strip biosensor for DNA analysis by hybridization", Anal. Chem, vol. 75, No. 16, pp. 4155-4160, (2003).
Liu, J., et al., "Optimization of a $Pb^{2+}$-directed gold nanoparticle/DNAzyme assembly and its application as a colorimetric biosensor for $Pb^{2+}$", Chem. Mater., vol. 16, No. 17, pp. 3231-3238, (2004).
Jones, K.D., et al., "Anniversary Essays, 3. Assay development, Changes in the development of rapid assays since 1995", Medical Devicelink, found at: http://www.devicelink.com/ivdt/archive/05/04/005.html, 3 pages, (2005).
Product Description: Pall Corporation, "Immunochromatographic, lateral flow or strip tests development ideas", found at: http://www.pall.com/34445_4154.asp, 7 pages, (1998).
Liu, J., et al., "Fast colorimetric sensing of adenosine and cocaine based on a general sensor design involving aptamers and nanoparticles", Angew. Chem. Int. Ed., vol. 45, pp. 90-94, (2006).
Liu, J., et al., "A simple and sensitive "dipstick" test in serum based on lateral flow separation of aptamer-linked nanostructures", Angewandte Chemie International Edition, vol. 45, pp. 7955-7959, (2006).
Jiang, P. et al., "Fluorescent detection of zinc in biological systems: recent development on the design of chemosensors and biosensors", Coordination Chemistry Reviews, vol. 248, pp. 205-229, (2004).
Lim, M.H. et al., "Metal-based turn-on fluorescent probes for sensing nitric oxide", Accounts of Chemical Research, vol. 40, No. 1, pp. 41-51, (2007).
Yoon, S. et al., "Screening mercury levels in fish with a selective fluorescent chemosensor", Journal of the American Chemical Society, vol. 127, pp. 16030-16031, (2005).
Yang, L. et al., "Imaging of the intracellular topography of copper with a fluorescent sensor and by synchrotron x-ray fluorescence microscopy", Proceedings of the National Academy of Science, vol. 102, No. 32, pp. 11179-11184, (2005).
He, Q. et al., "A selective fluorescent sensor for detecting lead in living cells", Journal of the American Chemical Society, vol. 128, pp. 9316-9317, (2006).
Zeng, L. et al., "A selective turn-on fluorescent sensor for imaging copper in living cells", Journal of the American Chemical Society, vol. 128, pp. 10-11, (2006).
Wegner, S.V. et al., "Design of an emission ratiometric biosensor from MerR family proteins: A sensitive and selective sensor for $Hg^{2+}$", Journal of the American Chemical Society, vol. 129, pp. 3474-3475, (2007).
Nolan, E.M. et al., "Turn-on and ratiometric mercury sensing in water with a red-emitting probe", Journal of the American Chemical Society, vol. 129, pp. 5910-5918, (2007).
Sasaki, D.Y. et al., "Metal-induced dispersion of lipid aggregates: A simple, selective, and sensitive fluorescent metal ion sensor", Angew. Chem. Int. Ed. England, vol. 34, No. 8, pp. 905-907, (1995).
Torrado, A. et al., "Exploiting polypeptide motifs for the design of selective Cu(II) ion chemosensors" Journal of the American Chemical Society, vol. 120, pp. 609-610, (1998).
Grandini, P. et al., "Exploiting the self-assembly strategy for the design of selective $Cu^{II}$ ion chemosensors", Angew. Chem. Int. Ed, vol. 38, No. 20, pp. 3061-3064, (1999).
Klein, G. et al., "A fluorescent metal sensor based on macrocyclic chelation", Chem. Comm., pp. 561-562, (2001).

Zheng, Y. et al., "A new fluorescent chemosensor for copper ions based on tripeptide glycyl-histidyl-lysine (GHK)", Organic Letters, vol. 3, No. 21, pp. 3277-3280, (2001).

Boiocchi, M. et al., "A two-channel molecular dosimeter for the optical detection of copper(II)" Chem. Comm, pp. 1812-1813, (2003).

Zheng, Y. et al., "Peptidyl fluorescent chemosensors for the detection of divalent copper", Analytical Chemistry, vol. 75, No. 7, pp. 1706-1712, (2003).

Zheng, Y. et al., "Development of fluorescent film sensors for the detection of divalent copper", Journal of the American Chemical Society, vol. 125, pp. 2680-2686, (2003).

Roy, B.C. et al., "Synthesis of new, pyrene-containing metal-chelating lipids and sensing of cupric ions", Organic Letters, vol. 5, No. 1, pp. 11-14, (2003).

Kaur, S. et al., "Photoactive chemosensors 4: a $Cu^{2+}$ protein cavity mimicking fluorescent chemosensor for selective $Cu^{2+}$ recognition", Tetrahedron Letters, vol. 45, pp. 5081-5085, (2004).

Mei, Y. et al., "A selective and sensitive chemosensor for $Cu^{2+}$ based on 8-hydroxyquinoline", Tetrahedron Letters, vol. 47, pp. 2447-2449, (2006).

Zhang, X-B. et al., "A highly selective fluorescent sensor for $Cu^{2+}$ based on 2-(2'-hydroxyphenyl)benzoxazole in a poly(vinyl chloride) matrix", Analytica Chimica Acta, vol. 567, pp. 189-195, (2006).

Comba, P. et al., "Synthesis of new phenanthroline-based heteroditopic ligands—highly efficient and selective fluorescence sensors for copper (II) ions", European Journal of Inorganic Chemistry, pp. 4442-4448, (2006).

Kim, S. H. et al., "$Hg^{2+}$-selective off-on and $Cu^{2+}$-selective on-off type fluoroionophore based upon cyclam", Organic Letters, vol. 8, No. 3, pp. 371-374, (2006).

White, B. R. et al., "Fluorescent peptide sensor for the selective detection of $Cu^{2+}$", Talanta, vol. 71, pp. 2015-2020, (2007).

Oter, O. et al., "Spectral characterization of a newly synthesized fluorescent semicarbazone derivative and its usage as a selective fiber optic sensor for copper(II)", Analytica Chimica Acta, vol. 584, pp. 308-314, (2007).

Dujols, V. et al., "A long-wavelength fluorescent chemodosimeter selective for Cu(II) ion in water", Journal of the American Chemical Society, vol. 119, pp. 7386-7387, (1997).

Yang, J-S. et al., "$Cu^{2+}$-induced blue shift of the pyrene excimer emission: a new signal transduction mode of pyrene probes", Organic Letters, vol. 3, No. 6, pp. 889-892, (2001).

Kaur, S. et al., "Photoactive chemosensors 3: a unique case of fluorescence enhancement with Cu(II)", Chem. Comm., pp. 2840-2841, (2002).

Wu, Q. et al., "Catalytic signal amplification using a heck reaction. An example in the fluorescence sensing of Cu(II)", Journal of the American Chemical Society, vol. 126, pp. 14682-14683, (2004).

Royzen, M. et al., "Ratiometric displacement approach to Cu(II) sensing by fluorescence", Journal of the American Chemical Society, vol. 127, pp. 1612-1613, (2005).

Xu, Z. et al., "Ratiometric and selective fluorescent sensor for $Cu^{II}$ based on internal charge transfer (ICT)", Organic Letters, vol. 7, No. 5, pp. 889-892, (2005).

Wen, Z-C. et al., "A highly selective charge transfer fluoroionophore for $Cu^{2+}$", Chem. Commun., pp. 106-108, (2006).

Yang, H. et al., "Highly selective ratiometric fluorescent sensor for Cu(II) with two urea groups", Tetrahedron Letters, vol. 47, pp. 2911-2914, (2006).

Martinez, R. et al., "2-aza-1,3-butadiene derivatives featuring an anthracene or pyrene unit: highly selective colorimetric and fluorescent signaling of $Cu^{2+}$ cation", Organic Letters, vol. 8, No. 15, pp. 3235-3238, (2006).

Navani, N.K. et al., "Nucleic acid aptamers and enzymes as sensors", Current Opinion in Chemical Biology, vol. 10, pp. 272-281, (2006).

Liu, J. et al., "A catalytic beacon sensor for uranium with parts-per-trillion sensitivity and millionfold selectivity", Proceedings of the National Academy of Science, vol. 104, No. 7, pp. 2056-2061, (2007).

Georgopoulos, P.G. et al., "Environmental copper: its dynamics and human exposure issues", Journal of Toxicology and Environmental Health, Part B, vol. 4, pp. 341-394, (2001).

Hertzberg, R.P. et al., "Cleavage of DNA with methidiumpropyl-EDTA-iron(II): reaction conditions and product analyses", Biochemistry, vol. 23, pp. 3934-3945, (1984).

Yazzie, M. et al., "Uranyl acetate causes DNA single strand breaks in vitro in the presence of ascorbate (Vitamin C)", Chem. Res. Toxicol., vol. 16, pp. 524-530, (2003).

Bolletta, F. et al., "A [$Ru^{II}$ $(bipy)_3$]-[1,9-diamino-3,7-diazanonane-4,6-dione] two-component system as an efficient on-off luminescent chemosensor for $Ni^{2+}$ and $Cu^{2+}$ in water, based on an ET (energy transfer) mechanism", Journal of the Chemical Society, Dalton Transactions, pp. 1381-1385, (1999).

Carmi, N. et al., "Characterization of a DNA-cleaving deoxyribozyme", Bioorganic & Medicinal Chemistry, vol. 9, issue 10, pp. 2589-2600, (2001).

Liu, J. et al., "A DNAzyme catalytic beacon sensor for paramagnetic $Cu^{2+}$ ions in aqueous solution with high sensitivity and selectivity", Journal of the American Chemical Society, vol. 129, No. 32, pp. 9838-9839, (2007), ASAP Web Release Date: Jul. 24, 2007.

Tanaka, K. et al., "Programmable self-assembly of metal ions inside artificial DNA duplexes", Nature Nanotechnology, vol. 1, pp. 190-194, (2006).

Achenbach, J.C. et al., "DNAzymes: From creation in vitro to application in vivo", Current Pharmaceutical Biotechnology, vol. 5, pp. 321-336, (2004).

Balaji, T. et al., "Optical sensor for the visual detection of mercury using mesoporous silica anchoring porphyrin moiety", The Analyst, vol. 130, pp. 1162-1167, (2005).

Caballero, A. et al., "Highly selective chromogenic and redox or fluorescent sensors of $Hg^{2+}$ in aqueous environment based on 1,4-disubstituted azines", Journal of the American Chemical Society, vol. 127, pp. 15666-15667, (2005).

Chan, W.H. et al., "Development of a mercury ion-selective optical sensor based on fluorescence quenching of 5,10,15,20-tetraphenylporphyrin", Analytica Chimica Acta, vol. 444, pp. 261-269, (2001).

Chen, P. et al., "A general strategy to convert the merR family proteins into highly sensitive and selective fluorescent biosensors for metal ions", Journal of the American Chemical Society, vol. 126, pp. 728-729, (2004).

Chiuman, W. et al., "Efficient signaling platforms built from a small catalytic DNA and doubly labeled fluorogenic substrates", Nucleic Acids Research, vol. 35, No. 2, pp. 401-405, (2007).

Cruz, R.P.G. et al., "Dinucleotide junction cleavage versatility of 8-17 deoxyribozyme", Chemistry & Biology, vol. 11, pp. 57-67, (2004).

Frasco, M.F. et al., "Mechanisms of cholinesterase inhibition by inorganic mercury", the FEBS Journal, vol. 274, pp. 1849-1861, (2007).

Guo, X. et al., "A highly selective and sensitive fluorescent chemosensor for $Hg^{2+}$ in neutral buffer aqueous solution", The Jouranl of the American Chemical Society, vol. 126, pp. 2272-2273, (2004).

Harris, H.H. et al., "The chemical form of mercury in fish", Science, vol. 301, pp. 1203, (2003).

Ha-Thi, M-H. et al., "Highly selective and sensitive phosphane sulfide derivative for the detection of $Hg^{2+}$ in an organoaqueous medium", Organic Letters, vol. 9, No. 6, pp. 1133-1136, (2007).

Joyce, G.F. et al., "Directed evolution of nucleic acid enzymes", Annual Review Biochem., vol. 73, pp. 791-836, (2004).

Ko, S-K. et al., "In vivo monitoring of mercury ions using a rhodamine-based molecular probe", Journal of the American Chemical Society, vol. 128, pp. 14150-14155, (2006).

Kuswandi, B. et al., "Capillary optode: determination of mercury(II) in aqueous solution", Analytical Letters, vol. 32, No. 9. 4, pp. 649-664, (1999).

Kuswandi, B. et al., "Selective pool optode for mercury ion sensing in aqueous solution", Sensors and Actuators B, vol. 74, pp. 131-137, (2001).

Lee, J-S. et al., "Colorimetric detection of mercuric ion ($Hg^{2+}$) in aqueous media using DNA-functionalized gold nanoparticles", Angewandte Chemie International Edition, vol. 46, pp. 4093-4096, (2007).

Liu, B. et al., "A selective fluorescent ratiometric chemodosimeter for mercury ion", Chem. Communications, pp. 3156-3158, (2005).

Liu, J. et al., "Fluorescent DNAzyme biosensors for metal ions based on catalytic molecular beacons", Methods in Molecular Biology, vol. 335, pp. 275-288, (2006).

Matsushita, M. et al., "A blue fluorescent antibody-cofactor sensor for mercury", Organic Letters, vol. 7, No. 22, pp. 4943-4946, (2005).

Miyake, Y. et al., "Mercury$^{II}$-mediated formation of thymine-Hg$^{II}$-thymine base pairs in DNA duplexes", Journal of the American Chemical Society, vol. 128, No. 7, pp. 2172-2173, (2006).

Nolan, E.M. et al., "A "turn-on" fluorescent sensor for the selective detection of mercuric ion in aqueous media", Journal of the American Chemical Society, vol. 125, pp. 14270-14271, (2003).

Ono, A. et al., "Highly selective oligonucleotide-based sensor for mercury (II) in aqueous solutions", Angew. Chem. Int. Ed., vol. 43, pp. 4300-4302, (2004).

Ostatna, V. et al., "Self-assembled monolayers of thiol-end-labeled DNA at mercury electrodes", Langmuir, vol. 22, pp. 6481-6484, (2006).

Prodi, L. et al., "An effective fluorescent achemosensor for mercury ions", Journal of the American Chemical Society, vol. 122, No. 28, pp. 6769-6770, (2000).

Silverman, S.K., "Survey and Summary: In vitro selection, characterization, and application of deoxyribozymes that cleave RNA", Nucleic Acids Research, vol. 33, No. 19, pp. 6151-6163, (2005).

Song, K.C. et al., "Fluorogenic Hg$^{2+}$-selective chemodosimeter derived from 8-hydroxyquinoline", Organic Letters, vol. 8, No. 16, pp. 3413-3416, (2006).

Szurdoki, F. et al., "A combinatorial approach to discover new chelators for optical metal ion sensing", Analytical Chemistry, vol. 72, No. 21, pp. 5250-5257, (2000).

Tanaka, Y. et al., "$^{15}$N-$^{15}$N J-coupling across Hg$^{II}$: Direct observation of Hg$^{II}$-mediated T-T base pairs in a DNA duplex" Journal of the American Chemical Society, vol. 129, No. 2, pp. 244-245, (2007).

Jacoby, M. "Mercury Sensor—Analytical Chemistry: Colorimetric method is sensitive and selective", Chemical & Engineering News, pp. 15, May 7, 2007.

Vannela, R. et al., "In vitro selection of Hg (II) and as (V)-dependent RNA-cleaving DNAzymes", Environmental Engineering Science, vol. 24, No. 1, pp. 73-84, (2007).

Vaughan, A.A. et al., "Optical fibre reflectance sensors for the detection of heavy metal ions based on immobilized Br-PADAP", Snesors and Actuators B, vol. 51, pp. 368-376, (1998).

Virta, M. et al., "A luminescence-based mercury biosensor", Analytical Chemistry, vol. 67, No. 3, pp. 667-669, (1995).

Wang, J. et al., "Detecting Hg$^{2+}$ ions with an ICT fluorescent sensor molecule: Remarkable emission spectra shift and unique selectivity", Journal of Organic Chemistry, vol. 71, pp. 4308-4311, (2006).

Wang, J. et al., "A series of polyamide receptor based PET fluorescent sensor molecules: Positively cooperative Hg$^{2+}$ ion binding with high sensitivity", Organic Letters, vol. 8, No. 17, pp. 3721-3724, (2006).

Widmann, A. et al., "Mercury detection in seawater using a mercaptoacetic acid modified gold microwire electrode", Electroanalysis, vol. 17, No. 10, pp. 825-831, (2005).

Xiao, Y. et al., "Electrochemical detection of parts-per-billion lead via an electrode-bound DNAzyme assembly", Journal of the American Chemical Society, vol. 129, pp. 262-263, (2007).

Yang, W. et al., "Solid phase extraction and spectrophotometric determination of mercury in tobacco and tobacco additives with 5-(p-aminobenzylidene)-thiothiorhodanine", Journal of the Brazilian Chemical Society, vol. 17, No. 5, pp. 1039-1044, (2006).

Yang, Y-K. et al., "A rhodamine-based fluorescent and colorimetric chemodosimeter for the rapid detection of Hg2+ ions in aqueous media", Journal of the American Chemical Society, vol. 127, pp. 16760-16761, (2005).

Zhang, X-B. et al "An optical fiber chemical sensor for mercury ions based on a porphyrin dimmer", Analytical Chemistry, vol. 74, No. 4, pp. 821-825, (2002).

Zhao, Y. et al., "A "turn-on" fluorescent sensor for selective Hg(II) detection in aqueous media based on metal-induced dye formation", Inorganic Chemistry, vol. 45, No. 25, pp. 10013-10015, (2006).

Zhao, Y. et al., "Tuning the sensitivity of a foldamer-based mercury sensor by its folding energy", Journal of the American Chemical Society, vol. 128, No. 31, pp. 9988-9989, (2006).

Zhao, Y. at al., "Detection of Hg2+ in aqueous solutions with a foldamer-based fluorescent sensor modulated by surgactant micelles", Organic Letters, vol. 8, No. 21, pp. 4715-4717, (2006).

Zuker, M., "Mfold web server for nucleic acid folding and hybridization prediction", Nucleic Acids Research, vol. 31, No. 13, pp. 3406-3415, (2003).

International Search Report dated May 10, 2007 for PCT application No. PCT/US2006/030617.

Liu, J. et al., "Adenosine-dependent assembly of aptazyme-functionalized gold nanoparticles and its application as a colorimetric biosensor", Analytical Chemistry, vol. 76, No. 6, pp. 1627-1632, (2004).

Liu, J. et al., "Smart nanomaterials responsive to multiple chemical stimuli with controllable cooperativity", Advanced Materials, vol. 18, No. 13, pp. 1667-1671, (2006).

Nutiu, R. et al., "Signaling aptamers for monitoring enzymatic activity and for inhibitor screening", Chembiochem—A European Journal of Chemical Biology, vol. 5, No. 8, pp. 1139-1144, (2004).

Nutiu, R. et al., "Structure-switching signaling aptamers: Transducing molecular recognition into fluorescence signaling", Chemistry—A European Journal, vol. 10, No. 8, pp. 1868-1876, (2004).

International Search Report dated Jul. 31, 2007 for PCT application No. PCT/US2007/064055.

Ahern, H., "Biochemical, reagent kits offer scientists good return on investment", The Scientist, vol. 9, No. 15, pp. 20-22, (1995).

Homann, M. et al., "Dissociation of long-chain duplex RNA can occur via strand displacement in vitro: biological implication", Nucleic Acids Research, vol. 24, No. 22, pp. 4395-4400, (1996).

Alivisatos, A.P. et al., "Quantum dots as cellular probes", Annual Review Biomed. Eng, vol. 7, pp. 55-76, (2005).

Dyadyusha, L. et al., "Quenching of CdSe quantum dot emission, a new approach for biosensing", Chemical Communication, pp. 3201-3203, (2005).

Ellington, A.D. et al., "In vitro selection of RNA molecules that bind specific ligands", Nature, vol. 346, pp. 818-822, (1990).

Gerion, D. et al., "Room-temperature single-nucleotide polymorphism and multiallele DNA detection using fluorescent nanocrystals and microarrays", Analytical Chemistry, vol. 75, No. 18, pp. 4766-4772, (2003).

Goldman, E.R. et al., "Multiplexed toxin analysis using four colors of quantum dot fluororeagents", Analytical Chemistry, vol. 76, No. 3, pp. 684-688, (2004).

Gueroui, Z. et al., "Single-molecule measurements of gold-quenched quantum dots", Physical Review Letters, vol. 93, No. 16, pp. 166108/1-166108/4, (2004).

Han, M. et al., "Quantum-dot-tagged microbeads for multiplexed optical coding of biomolecules", Nature Biotechnology, vol. 19, pp. 631-635, (2001).

Hansen, J.A. et al., "Quantum-dot/Aptamer-based ultrasensitive multi-analyte electrochemical biosensor", Journal of the American Chemical Society, vol. 128, No. 7, pp. 2228-2229, (2006).

Hartig, J.S. et al., "Protein-dependent ribozymes report molecular interactions in real time", Nature Biotechnology, vol. 20, pp. 717-722, (2002).

Herman, T. et al., "Adaptive recognition by nucleic acid aptamers", Science, vol. 287, pp. 820-825, (2000).

Kurreck, J., "Antisense technologies Improvement through novel chemical modifications", Eur. J. Biochem, vol. 270, pp. 1628-1644, (2003).

Lee, J.F. et al., "Aptamer database", Nucleic Acids Research, vol. 32, Database Issue, pp. D95-D100, (2004).

Levy, M. et al., "Quantum-dot aptamer beacons for the detection of proteins", ChemBioChem, vol. 6, pp. 2163-2166, (2005).

Liu, J. et al., "Preparation of aptamer-linked gold nanoparticle purple aggregates for colorimetric sensing of analytes", Nature Protocols, vol. 1, No. 1, pp. 246-252, (2006).

Medintz, I.L. et al., "Quantum dot bioconjugates for imaging, labeling and sensing", Nature Materials, vol. 4, pp. 435-446, (2005).

Miduturu, C. V. et al., "Modulation of DNA constraints that control macromolecular folding", Angew. Chem. Int. Ed., vol. 45, pp. 1918-1921, (2006).

Mitchell, G.P. et al., "Programmed assembly of DNA functionalized quantum dots", Journal of the American Chemical Society, vol. 121, No. 35, pp. 8122-8123, (1999).

Nutiu, R. et al., "Structure-switching signaling aptamers: Transducing molecular recognition into fluorescence signaling", Chem. Eur. J., vol. 10, pp. 1868-1876, (2004).

Oh, E. et al., "Inhibition assay of biomolecules based on fluorescence resonance energy transfer (FRET) between quantum dots and gold nanoparticles", Journal of the American Chemical Society, vol. 127, No. 10, pp. 3270-3271, (2005).

Rajendran, M. et al., "In vitro selection of molecular beacons", Nucleic Acids Research, vol. 31, No. 19, pp. 5700-5713, (2003).

Vet, J.A.M. et al., "Multiplex detection of four pathogenic retroviruses using molecular beacons", Proceedings of the National Academy of Science, USA., vol. 96, pp. 6394-6399, (1999).

Wargnier, R. et al., "Energy transfer in aqueous solutions of oppositely charged CdSe/ZnS core/shell quantum dot-nanogold assemblies", Nano Letters, vol. 4, No. 3, pp. 451-457, (2004).

Wilson, R. et al., "Encoded microcarriers for high-throughput multiplexed detection", Angewandte Chemie International Edition, vol. 45, pp. 6104-6117, (2006).

Winkler, W.C. et al., "Regulation of bacterial gene expression by riboswitches", The Annual Review of Microbiology, vol. 59, pp. 487-517, (2005).

Yang, C.J. et al., "Light-switching excimer probes for rapid protein monitoring in complex biological fluids", PNAS, vol. 102, No. 48, pp. 17278-17283, (2005).

Liu, J. et al., "Quantum dot encoding of aptamer-linked nanostructures for one-pot simultaneous detection of multiple analytes", Analytical Chemistry, vol. 79, No. 11, pp. 4120-4125, (2007).

Lu, Y. et al., "Smart nanomaterials inspired by biology: Dynamic assembly of error-free nanomaterials in response to multiple chemical and biological stimuli", Accounts of Chemical Research, vol. 40, No. 5, pp. 315-323, (2007).

Allen, M.J. et al., "Magnetic resonance contrast agents for medical and molecular imaging", Met. Ions Biol. Syst., vol. 42, pp. 1-38, (2004).

Artemov, D. et al., "MR molecular imaging of the Her-2/neu receptor in breast cancer cells using targeted iron oxide nanoparticles", Magnetic Resonance in Medicine, vol. 49, pp. 403-408, (2003).

Buerger, C. et al., "Sequence-specific peptide aptamers, interacting with the intracellular domain of the epidermal growth factor receptor, interfere with stat3 activation and inhibit the growth of tumor cells", The Journal of Biological Chemistry, vol. 278, No. 39, pp. 37610-37621, (2003).

Buerger, C. et al., "Bifunctional recombinant proteins in cancer therapy: cell penetrating peptide aptamers as inhibitors of growth factor signaling", J. Cancer Research Clin. Oncol., vol. 129, pp. 669-675, (2003).

Carr, D.H. et al., "Gadolinium—DTPA as a contrast agent in MRI: initial clinical experience in 20 patients", American Journal of Roentfenol., vol. 143, pp. 215-224, (1984).

Chen, Y. et al., "An autonomous DNA nanomotor powered by a DNA enzyme", Angew. Chem. Int. Ed., vol. 43, pp. 3554-3557, (2004).

Corot, C. et al., "Macrophage imaging in central nervous system and in carotid atherosclerotic plaque using ultrasmall superparamagnetic iron oxide in magnetic resonance imaging", Investigative Radiology, vol. 39, No. 10, pp. 619-625, (2004).

Dodd, C.H. et al., "Normal T-cell response and in vivo magnetic resonance imaging of T cells loaded with HIV transactivator-peptide-derived superparamagnetic nanoparticles", Journal of Immunological Methods, vol. 256, pp. 89-105, (2001).

Drolet, D.W. et al., "An enzyme-linked oligonucleotide assay", Nature Biotechnology, vol. 14, pp. 1021-1025, (1996).

Enochs, W.S. et al., "Improved delineation of human brain tumors on MR images using a long-circulating, superparamagnetic iron oxide agent", Journal of Magnetic Resonance Imaging, vol. 9, pp. 228-232, (1999).

Famulok, M. et al., "Nucleic acid aptamers-from selection in vitro to applications in vivo", Accounts of Chemical research, vol. 33, No. 9, pp. 591-599, (2000).

Fang, X. et al., "Molecular aptamer for real-time oncoprotein platelet-derived growth factor monitoring by fluorescence anisotropy", Analytical Chemistry, vol. 73, No. 23, pp. 5752-5757, (2001).

Frullano, L. et al., "Synthesis and characterization of a doxorubicin-Gd(III) contrast agent conjugate: A new approach toward prodrug-procontrast complexes", Inorganic Chemistry, vol. 45, No. 21, pp. 8489-8491, (2006).

Hamaguchi, N. et al., "Aptamer beacons for the direct detection of proteins", Analytical Biochemistry, vol. 294, pp. 126-131, (2001).

Harisinghani, M.G. et al., "Noninvasive detection of clinically occult lymph-node metastases in prostate cancer", The New England Journal of Medicine, vol. 348, No. 25, pp. 2491-2499, (2003).

Hermann, T. et al., "Adaptive recognition by nucleic acid aptamers", Science, vol. 287, pp. 820-825, (2000).

Hoppe-Seyler, F. et al., "Peptide aptamers: Specific inhibitors of protein function", Current Molecular Medicine, vol. 4, pp. 529-538, (2004).

Huang, C-C. et al., "Aptamer-modified gold nanoparticles for colorimetric determination of platelet-derived growth factors and their receptors", Analytical Chemistry, vol. 77, No. 17, pp. 5735-5741, (2005).

Josephson, L. et al., "High-efficiency intracellular magnetic labeling with novel superparamagnetic-tat peptide conjugates", Bioconjugate Chem., vol. 10, No. 2, pp. 186-191, (1999).

Josephson, L. et al., "The effects of iron oxides on proton relaxivity", Magnetic Resonance Imaging, vol. 6, pp. 647-653, (1988).

Josephson, L. et al., "Magnetic nanosensors for the detection of oligonucleotide sequences", Angew. Chem. Int. Ed., vol. 40, No. 17, pp. 3204-3206, (2001).

Kabalka, G. et al., "Gadolinium-labeled liposomes: Targeted MR contrast agents for the liver and spleen", Radiology, vol. 163, pp. 255-258, (1987).

Kooi, M.E. et al., "Accumulation of ultrasmall superparamagnetic particles of iron oxide in human atherosclerotic plaques can be detected by in vivo magnetic resonance imaging", Circulation, vol. 107, pp. 2453-2458, (2003).

Kresse, M. et al., "Targeting of ultrasmall superparamagnetic iron oxide (USPIO) particles to tumor cells in vivo by using transferring receptor pathways", Magn. Reson. Med., vol. 40, pp. 236-242, (1998).

Lee, J. et al., "A steroid-conjugated contrast agent for magnetic resonance imaging of cell signaling", Journal of American Chemical Society, vol. 127, No. 38, pp. 13164-13166, (2005).

Lewin, M. et al., "Tat peptide-derivatized magnetic nanoparticles allow in vivo tracking and recovery of progenitor cells", Nature Biotechnology, vol. 18, pp. 410-414, (2000).

Li, J.J. et al., "Molecular aptamer beacons for real-time protein recognition", Biochemical and Biophysical Research Communications, vol. 292, No. 1, pp. 31-40, (2002).

Li, W-H. et al., "A calcium-sensitive magnetic resonance imaging contrast agent", Journal of the American Chemical Society, vol. 121, No. 6, pp. 1413-1414, (1999).

Lin, C.H. et al., "Structural basis of DNA folding and recognition in an AMP-DNA aptamer complex: distinct architectures but common recognition motifs for DNA and RNA aptamers complexed to AMP", Chemistry and Biology, vol. 4, pp. 817-832, (1997).

Liss, M. et al., "An aptamer-based quartz crystal protein biosensor", Analytical Chemistry, vol. 74, No. 17, pp. 4488-4495, (2002).

Liu, Y. et al., "Aptamer-directed self-assembly of protein arrays on a DNA nanostructure", Angew. Chem. Int. Ed., vol. 44, pp. 4333-4338, (2005).

Macaya, R.F. et al., "Thrombin-binding DNA aptamer forms a unimolecular quadruplex structure in solution", Proceedings of the National Academy of Science USA, vol. 90, pp. 3745-3749, (1993).

Nagel-Wolfrum, K. et al., "The interaction of specific peptide aptamers with the DNA binding domain and the dimerization domain of the transcription factor stat3-inhibits transactivation and induces apoptosis in tumor cells", Molecular Cancer Research, vol. 2, pp. 170-182, (2004).

Nitin, N. et al., "Functionalization and pepride-based delivery of magnetic nanoparticles as an intracellular MRI contrast agent", J. Biol. Inorg. Chem., vol. 9, pp. 706-712, (2004).

Nutiu, R. et al., "Engineering DNA aptamers and DNA enzymes with fluorescence-signaling properties", Pure Appl. Chem., vol. 76, Nos. 7-8, pp. 1547-1561, (2004).

Padmanabhan, K. et al., "The structure of a-thrombin inhibited by a 15-mer single-stranded DNA aptamer", The Journal of Biological Chemistry, vol. 268, No. 24, pp. 17651-17654, (1993).

Pavlov, V. et al., "Aptamer-functionalized au nanoparticles for the amplified optical detection of thrombin", The Journal of the American Chemical Society, vol. 126, No. 38, pp. 11768-11769, (2004).

Pendergrast, P.S. et al., "Nucleic acid aptamers for target validation and therapeutic applications", Journal of Biomolecular Techniques, vol. 16, issue 3, pp. 224-234, (2005).

Perez, J.M. et al., "Use of magnetic nanoparticles as nanosensors to probe for molecular interactions", ChemBioChem, vol. 5, pp. 261-264, (2004).

Perez, J.M. et al., "Viral-induced self-assembly of magnetic nanoparticles allows the detection of viral particles in biological media", Journal of the American Chemical Society, vol. 125, No. 34, pp. 10192-10193, (2003).

Radi, A-E. et al., "Reagentless, reusable, ultrasensitive electrochemical molecular beacon aptasensor", Journal of the American Chemical Society, vol. 128, No. 1, pp. 117-124, (2006).

Saeed, M. et al., "Occlusive and reperfused myocardial infarcts: differentiation with Mn-DPDP-enhanced MR imaging", Radiology, vol. 172, pp. 59-64, (1989).

Shen, T. et al., "Monocrystalline iron oxide nanocompounds (MION): Physicochemical properties", Magn. Reson. Med., vol. 29, pp. 599-604, (1993).

Soriaga, M.P. et al., "Determination of the orientation of adsorbed molecules at solid-liquid interfaces by thin-layer electrochemistry: Aromatic compounds at platinum electrodes", Journal of the American Chemical Society, vol. 104, pp. 2735-2742, (1982).

Soriaga, M.P. et al., "Determination of the orientation of aromatic molecules adsorbed on platinum electrodes: The influence of iodide a surface-active anion", Journal of the American Chemical Society, vol. 104, pp. 2742-2747, (1982).

Soriaga, M.P. et al., "Determination of the orientation of aromatic molecules adsorbed on platinum electrodes: The effect of solute concentration", Journal of the American Chemical Society, vol. 104, pp. 3937-3945, (1982).

Sosnovik, D.E. et al., "Emerging concepts in molecular MRI", Current Opinion in Biotechnology, vol. 18, pp. 4-10, (2007).

Taboada, E. et al., "Relaxometric and magnetic characterization of ultrasmall iron oxide nanoparticles with high magnetization. Evaluation as potential $T_1$ magnetic resonance imaging contrast agents for molecular imaging", Langmuir, vol. 23, No. 8, pp. 4583-4588, (2007).

Tasset, D.M. et al., "Oligonucleotide inhibitors of human thrombin that bind distinct epitopes", J. Mol. Biol., vol. 272, pp. 688-698, (1997).

Tian, Y. et al., "DNAzyme amplification of molecular beacon signal", Talanta, vol. 67, pp. 532-537, (2005).

Tompkins, H.G. et al., "The study of the gas-solid interaction of acetic acid with a cuprous oxide surface using reflection-absorption spectroscopy", Journal of colloid and interface science, vol. 49, No. 3, pp. 410-421, (1974).

Tsourkas, A. et al., "Magnetic relaxation switch immunosensors detect enantiomeric impurities", Angew. Chem. Int. Ed., vol. 43, pp. 2395-2399, (2004).

Wang, S. et al., "Core/shell quantum dots with high relaxivity and photoluminescence for multimodality imaging", Journal of the American Chemical Society, vol. 129, No. 13, pp. 3848-3856, (2007).

Weissleder, R. et al., "MR imaging of splenic metastases: Ferrite-enhanced detection in rats", American Journal Roentgenol., vol. 149, pp. 723-726, (1987).

Xiao, Y. et al., "Label-free electronic detection of thrombin in blood serum by using an aptamer-based sensor", Angew. Chem. Int. Ed., vol. 44, pp. 5456-5459, (2005).

Xiao, Y. et al., "A reagentless signal-on architecture for electronic, aptamer-based sensors via target-induced strand displacement", Journal of the American Chemical Society, vol. 127, No. 51, pp. 17990-17991, (2005).

Xu, D. et al., "Label-free electrochemical detection for aptamer-based array electrodes", Analytical Chemistry, vol. 77, No. 16, pp. 6218-6224, (2005).

Yamamoto, R. et al., "Molecular beacon aptamer fluoresces in the presence of Tat protein of HIV-1", Genes to Cells, vol. 5, pp. 389-396, (2000).

Zhao, M. et al., "Magnetic sensors for protease assays", Angew. Chem. Int. Ed., vol. 42, No. 12, pp. 1375-1378, (2003).

Zhao, M. et al., "Differential conjugation of tat peptide to superparamagnetic nanoparticles and its effect on cellular uptake", Bioconjugate Chem., vol. 13, pp. 840-844, (2002).

Liu, J. et al., "Colorimetric $Cu^{2+}$ detection with a ligation DNAzyme and nanoparticles", Chemical Communications, Advance Articles, DOI: 10.1039/b712421j, 6 pages, Oct. 24, 2007.

Liu, J. et al., "Non-Base pairing DNA provides a new dimension for controlling aptamer-linked nanoparticles and sensors", Journal of the American Chemical Society, vol. 129, No. 27, pp. 8634-8643, (2007).

Liu, J. et al., Supporting Information for "Colorimetric $Cu^{2+}$ detection with a ligation DNAzyme and nanoparticles", Chemical Communications, Advance Articles, 4 pages, Oct. 24, 2007.

Stratagene Catolog, "Gene Characterization Kits", 2 pages, (1988).

Fahlman, R.P. et al., "DNA conformational switches as sensitive electronic sensors of analytes", Journal of the American Chemical Society, vol. 124, 4610-4616, (2002).

Mayer, G. et al., "High-throughput-compatible assay for glmS riboswitch metabolite dependence", ChemBioChem, vol. 7, pp. 602-604, (2006).

Elowe, N., et al., "Small-molecule screening made simple for a difficult target with a signaling nucleic acid aptamer that reports on deaminase activity", Angew. Chem. Int. Ed., vol. 45, pp. 5648-5652, (2006).

Yigit, M. et al., "Smart "turn-on" magnetic resonance contrast agents based on aptamer-functionalized superparamagnetic iron oxide nanoparticles", ChemBioChem, vol. 8, pp. 1675-1678, (2007).

Xu, D. et al., "Label-free electrochemical detection for aptamer-based array electrodes", Analytical Chemistry, vol. 77, No. 16, pp. 5107-5113, (2005).

Yigit, M et al., "MRI detection of thrombin with aptamer functionalized superparamagnetic iron oxide nanoparticles", Bioconjugate Chem., vol. 19, pp. 412-417, (2008).

International Search Report dated Mar. 4, 2009 for PCT application No. PCT/US2008/070177.

International Search Report dated Apr. 17, 2009 for PCT application No. PCT/US2008/051185.

International Search Report dated Aug. 13, 2009 for PCT application No. PCT/US2008/072327.

Liu, J. et al., "Rational design of turn-on allosteric DNAzyme catalytic beacons for aqueous mercury ions with ultrahigh sensitivity and selectivity", Angewandte Chemmie. International Edition, vol. 46, No. 40, pp. 7587-7590, (2007).

Stadler, B. et al., "Micropatterning of DNA-tagged vesicles", Langmuir, vol. 20, No. 26, pp. 11348-11354, (2004).

Pfeiffer, I. et al., "Bivalent cholesterol-Based coupling of oligonucletides to lipid membrane assemblies", Journal of the American Chemical Society, vol. 126, No. 33, pp. 10224-10225, (2004).

Shin, J. et al., "Acid-triggered release via dePEGylation of DOPE liposomes containing acid-labile vinyl ether PEG-lipids", Journal of Controlled Release, vol. 91, issues 1-2, pp. 187-200, (2003).

Cram, D.J. et al., "Organic Chemistry", Mcgraw-Hill, pp. 560-569, (1959).

Rusconi, C.P. et al., "Antidote-mediated control of an anticoagulant aptamer in vivo", Nature Biotechnology Letters, vol. 22, No. 11, pp. 1423-1428, (2004).

Willis M.C. et al., "Liposome-anchored vascular endothelial growth factor aptamers", Bioconjugate Chem., vol. 9, No. 5, pp. 573-582, (1998).

Healy, J.M. et al., "Pharmacokinetics and biodistribution of novel aptamer compositions", Pharm. Research, vol. 21, No. 12, pp. 2234-2246, (2004).

Farokhzad, O.C. et al., "Targeted nanoparticle-aptamer bioconjugates for cancer chemotherapy in vivo", Proceedings of the National Academy of Science, vol. 103, No. 16, pp. 6315-6320, (2006).

Farokhzad, O.C. et al., "Nanopartide-aptamer bioconjugates: A new approach for targeting prostate cancer cells", Cancer Research, vol. 64, pp. 7668-7672, (2004).

American Cancer Society Statistics for 2006. http://www.cancer.org/docroot/stt/stt_0.asp 2006.

Eifel, P. et al., "National Institutes of Health Consensus Development Panel, National Institutes of Health Consensus Development Conference statement: Adjuvant therapy for breast cancer, Nov. 1-3, 2000", Journal of the National Cancer Institute, vol. 93, No. 13, pp. 979-989, (2001).

Park, J.W. et al., "Tumor targeting using anti-her2 immunoliposomes", Journal of Controlled Release, vol. 74, pp. 95-113, (2001).

Kallab, V. et al., "HER2/EGFR internalization: a novel biomarker for ErbB-targeted therapeutics", Breast Cancer Research Treat., vol. 88, pp. S126-S127, (2004).

Wilson, K.S. et al., "Differential gene expression patterns in HER2/neu-positive and -negative breast cancer cell lines and tissues", American Journal of Pathology, vol. 161, No. 4, pp. 1171-1185, (2002).

Weigelt, B. et al., "Breast cancer metastasis: Markers and models", Nature Reviews, Cancer, vol. 5, pp. 591-602, (2005).

Pegram, M.D. et al., "Rational combinations of trastuzumab with chemotherapeutic drugs used in the treatment of breast cancer", Journal of the National Cancer Institute, vol. 96, No. 10, pp. 739-749, (2004).

Kirpotin, D.B. et al., "Antibody targeting of long-circulating lipidic nanoparticles does not increase tumor localization but does increase internalization in animal models", Cancer Research, vol. 66, No. 13, pp. 6732-6740, (2006).

Cheng, C. et al., "Formulation of Functionalized PLGA-PEG Nanoparticles for in Vivo Targeted Drug Delivery", Biomaterials, vol. 28, issue 5, pp. 869-876, (2007).

Bass, B.L. et al., "Specific interaction between the self-splicing RNA of Tetrahymena and its guanosine substrate: implications for biological catalysis by RNA", Nature, vol. 308, pp. 820-826, (1984).

Ellington, A.D. et al., "Combinatorial methods: aptamers and aptazymes", Part of the SPIE Conference on Advanced Materials and Opitical Systems for Chemical and Biological Detection, SPIE, vol. 3858, pp. 126-134, (1999).

Robertson, M.P. et al., "Aptazymes as generalized signal transducers", Nucleic Acids Symp. Ser., vol. 41, pp. 1-3, (1999).

Pagratis, N.C. et al., "Potent 2'-amino-, and 2'-fluoro-2'-deoxyribonucleotide RNA inhibitors of keratinocyte growth factor", Nature Biotechnology, vol. 15, pp. 68-73, (1997).

Lupold, S.E. et al., "Identification and characterization of nuclease-stabilized RNA molecules that bind human prostate cancer cells via the prostate-specific membrane antigen", Cancer research, vol. 62, pp. 4029-4033, (2002).

Jenison, R.D. et al., "Oligonucleotide inhibitors of P-selectin-dependent neutrophil-platelet adhesion", Antisense Nucleic Acid Drug Dev., vol. 8, pp. 265-279, (1998).

Hicke, B.J. et al., "DNA aptamers block L-selectin function in vivo. Inhibition of human lymphocyte trafficking in SCID mice", J. Clinical Invest., vol. 98, No. 12, pp. 2688-2692, (1996).

O'Connell, D. et al., "Calcium-dependent oligonucleotide antagonists specific for L-selectin", Proceedings of the National Academy of Science, U.S.A., vol. 93, pp. 5883-5887, (1996).

Soukup, G.A. et al., "Design of allosteric hammerhead ribozymes activated by ligand-induced structure stabilization", Structure, vol. 7, pp. 783-791, (1999).

Straubinger, R.M. et al., "Preparation and characterization of taxane-containing liposomes", Methods in Enzymology, vol. 391, pp. 97-117, (2005).

Rivera, E. "Liposomal anthracyclines in metastatic breast cancer: Clinical update", The Oncologist, vol. 8, supplement 2, pp. 3-9, (2003).

Kornblith, P. et al., "Breast cancer—Response rates to chemotherapeutic agents studied in vitro", Anticancer Research, vol. 23, pp. 3405-3411, (2003).

Pei, J. et al., "Combination with liposome-entrapped, ends-modified raf antisense oligonucleotide (LErafAON) improves the anti-tumor efficacies of cisplatin, epirubicin, mitoxantrone, docetaxel and gemcitabine", Anti-Cancer Drugs, vol. 15, pp. 243-253, (2004).

Allen, T.M. et al., "Therapeutic opportunities for targeted liposomal drug delivery", Advanced Drug Delivery Reviews, vol. 21, pp. 117-133, (1996).

Hofheinz, R.D. et al., "Liposomal encapsulated anti-cancer drugs", Anti-Cancer Drugs, vol. 16, pp. 691-707, (2005).

Schluep, T. et al., "Preclinical efficacy of the camptothecin-polymer conjugate IT-101 in multiple cancer models", Clinical Cancer Research, vol. 12, No. 5, pp. 1606-1614, (2006).

Schluep, T. et al., "Pharmacokinetics and biodistribution of the camptothecin-polymer conjugate IT-101 in rats and tumor-bearing mice", Cancer Chemoth. Pharm., vol. 57, pp. 654-662, (2006).

Cheng, J. et al., "Antitumor Activity of beta-Cyclodextrin Polymer-Camptothecin Conjugates", Molecular Pharmaceutics, vol. 1, No. 3, pp. 183-193, (2004).

Cheng, J. et al., "Synthesis of linear, beta-cyclodextrin-based polymers and their camptothecin conjugates", Bioconjugate Chem., vol. 14, pp. 1007-1017, (2003).

Guo, X. et al., "Steric stabilization of fusogenic liposomes by a low-pH sensitive PEG-diortho ester-lipid conjugate", Bioconjugate Chem., vol. 12, pp. 291-300, (2001).

Gerasimov, O.V. et al., "Cytosolic drug delivery using pH- and light-sensitive liposomes", Advanced Drug Delivery Reviews., vol. 38, pp. 317-338, (1999).

Rovira-Bru, M. et al., "Size and structure of spontaneously forming liposomes in lipid/PEG-lipid mixtures", Biophysical Journal, vol. 83, pp. 2419-2439, (2002).

Liu, J. et al., "Proofreading and error removal in a nanomaterial assembly", Angewandte Chemie, International Edition, vol. 44, pp. 7290-7293, (2005).

Liu, J. et al., "Design of asymmetric DNAzymes for dynamic control of nanoparticle aggregation states in response to chemical stimuli", Organic & Biomolecular Chemistry, vol. 4, pp. 3435-3441, (2006).

Cho, H.S. et al., "Structure of the extracellular region of HER2 alone and in complex with the Herceptin Fab", Nature, vol. 421, pp. 756-760, (2003).

Leahy, D.J. et al., "A Mammalian Expression Vector for Expression and Purification of Secreted Proteins for Structural Studies", Protein Expression and Purification, vol. 20, pp. 500-506, (2000).

Bartel, D.P. et al., "Isolation of new ribozymes from a large pool of random sequences", Science, vol. 261, pp. 1411-1418, (1993).

Jellinek, D. et al., "Inhibition of receptor binding by high-affinity RNA ligands to vascular endothelial growth factor", Biochemistry, vol. 33, pp. 10450-10456, (1994).

Jellinek, D. et al., "Potent 2'-Amino-2'-deoxypyrimidine RNA Inhibitors of Basic Fibroblast Growth Factor", Biochemistry, vol. 34, pp. 11363-11372, (1995).

Green, L.S. et al., "Inhibitory DNA Ligands to Platelet-Derived Growth Factor B-Chain", Biochemistry, vol. 35, pp. 14413-14424, (1996).

Lee, T.C. et al., "Overexpression of RRE-derived sequences inhibits HIV-1 replication in CEM cells", New Biologist, vol. 4, p. 66, (1992).

Lupoid, S.E. et al., "Identification and characterization of nuclease-stabilized RNA molecules that bind human prostate cancer cells via the prostate-specific membrane antigen", Cancer Research, vol. 62, pp. 4029-4033, (2002).

Andresen, T.L. et al., "Advanced strategies in liposomal cancer therapy: Problems and prospects of active and tumor specific drug release", Progress in Lipid Research, vol. 44, pp. 68-97, (2005).

Woodle, M.C. et al., "Sterically Stabilized Liposomes—Reduction in electrophoretic mobility but not electrostatic surface potential", Biophysical Journal, vol. 61, pp. 902-910, (1992).

Zalipsky, S. et al., "Long Circulating, Cationic Liposomes Containing Amino-Peg-Phosphatidylethanolamine", FEBS Letters, vol. 353, pp. 71-74, (1994).

Morrison, W., "A fast, simple and reliable method for the microdetermination of phosphorus in biological materials", Analytical Biochemistry, vol. 7, issue 2, pp. 218-224, (1964).

Kirpotin, D. et al., "Sterically Stabilized Anti-HER2 Immunoliposomes: Design and Targeting to Human Breast Cancer Cells in Vitro", Biochemistry, vol. 36, pp. 66-75, (1997).

Klibanov, A.L. et al., "Activity of Amphipathic Poly(Ethylene Glycol)-5000 to Prolong the Circulation Time of Liposomes Depends on the Liposome Size and is Unfavorable for Immunoliposome Binding to Target", Biochim. Biophys. Acta, vol. 1062, pp. 142-148, (1991).

Park, J.W. et al., "Development of Anti-P185$^{HER2}$ Immunoliposomes for Cancer-Therapy", Proceedings of the National Academy of Science U.S.A., vol. 92, pp. 1327-1331, (1995).

Zalipsky, S. "Synthesis of an End-Group Functionalized Polyethylene Glycol-Lipid Conjugate for Preparation of Polymer-Grafted Liposomes", Bioconjugate Chem., vol. 4, pp. 296-299, (1993).

Allen, T.M. et al., "A New Strategy for Attachment of Antibodies to Sterically Stabilized Liposomes Resulting in Efficient Targeting to Cancer-Cells", Biochimica et Biophysica Acta, vol. 1237, pp. 99-108, (1995).

Gillies, E.R. et al., "A new approach towards acid sensitive copolymer micelles for drug delivery", Chemical Communications, Issue 14, pp. 1640-1641, (2003).

Joensuu, O.I., "Fossil Fuels as a Source of Mercury Pollution", Science, vol. 172, No. 3987, pp. 1027-1028, (1971).

Malm, O., "Gold mining as a source of mercury exposure in the Brazilian Amazon", Environmental Research, vol. 77, No. 2, pp. 73-78, (1998).

Tchounwou, P.B. et al., "Environmental exposure to mercury and its toxicopathologic implications for public health", Environmental Toxicology, vol. 18, No. 3,pp. 149-175, (2003).

Yoon, S. et al., "A bright and specific fluorescent sensor for mercury in water, cells, and tissue", Angewandte Chemie International Edition, vol. 46, No. 35, pp. 6658-6661, (2007).

Liu, X.F. et al., "Optical detection of mercury(II) in aqueous solutions by using conjugated polymers and label-free oligonucleotides", Advanced Materials, vol. 19, No. 11, p. 1471, (2007).

Chiang, C.K. et al., "Oligonucleotide-based fluorescence probe for sensitive and selective detection of mercury (II) in aqueous solution", Analytical Chemistry, vol. 80, No. 10, pp. 3716-3721, (2008).

Yamini, Y. et al., "Solid phase extraction and determination of ultra trace amounts of mercury(II) using octadecyl silica membrane disks modified by hexathia-18-crown-6-tetraone and cold vapour atomic absorption spectrometry", Analytica Chimica Acta, vol. 355, issue 1, pp. 69-74, (1997).

Darbha, G.K. et al., "Gold nanoparticle-based miniaturized nanomaterial surface energy transfer probe for rapid and ultrasensitive detection of mercury in soil, water, and fish", Acs Nano, vol. 1, No. 3, pp. 208-214, (2007).

Li, D. et al., "Optical analysis of Hg2+ ions by oligonucleotide-gold-nanoparticle hybrids and DNA-based machines", Angewandte Chemie International Edition, vol. 47, No. 21, pp. 3927-3931, (2008).

Liu, C.W. et al., "Detection of mercury(II) based on Hg2+-DNA complexes inducing the aggregation of gold nanoparticles", Chemical Communications, vol. 19, pp. 2242-2244, (2008).

Xue, X. et al., "One-step, room temperature, colorimetric detection of mercury (Hg2+) using DNA/nanoparticle conjugates", Journal of the American Chemical Society, vol. 130, No. 11, pp. 3244-3245, (2008).

Wang, L. et al., "Gold nanoparticle-based optical probes for target-responsive DNA structures", Gold Bulletin, vol. 41, No. 1, pp. 37-41, (2008).

Clarkson, T.W. et al., "Mercury—Major Issues in Environmental-Health", Environmental Health Perspectives, vol. 100, pp. 31-38, (1993).

Wren, C.D. "A Review of Metal Accumulation and Toxicity in Wild Mammals, 1 Mercury", Environmental Research, vol. 40, No. 1, pp. 210-244, (1986).

Koos, B.J. et al., "Mercury Toxicity in Pregnant Woman, Fetus, and Newborn-Infant -Review", American Journal of Obstetrics and Gynecology, vol. 126, No. 3, pp. 390-409, (1976).

Yu, Y. et al., "p-dimethylaminobenzaldehyde thiosemicarbazone: A simple novel selective and sensitive fluorescent sensor for mercury(II) in aqueous solution", Talanta, vol. 69, No. 1, pp. 103-106, (2006).

Braman, R.S., "Membrane Probe—Spectral Emission Type Detection System for Mercury in Water", Analytical Chemistry, vol. 43, No. 11, pp. 1462-1467, (1971).

Wernette, D.P. et al., "Surface immobilization of catalytic beacons based on ratiometric fluorescent DNAzyme sensors: a systematic study", Langmuir, vol. 23, No. 18, pp. 9513-9521, (2007).

Wang, Z. et al., "Highly sensitive "turn-on" fluorescent sensor for Hg2+ in aqueous solution based on structure-switching DNA", Chemical Communications, pp. 6005-6007, (2008).

Lu, Y. "New catalytic DNA fluorescent and colorimetric sensors for on-sit and real-time monitoring of industrial and drinking water", ISTC Reports, Illinois Sustainable Technology Center Institute of Natural Resource Sustainability, University of Illinois at Urbana-Champaign, http://www.istc.illinois.edu/info/library_docs/RR/RR-114.pdf, pp. i-ix, and 1-30, (2009).

Turner, A. P. F., "Biochemistry: Biosensors—Sense and Sensitivity", Science, vol. 290, No. 5495, pp. 1315-1317, (2000).

Abbasi, S. A., "Atomic absorption spectrometric and spectrophotometric trace analysis of uranium in environmental samples with n-p-methoxyphenyl-2-4-(2-pyridylazo) resorcinol", Int. J. Environ. Anal. Chem., vol. 36, pp. 163-172, (1989).

Arnez, J. G. et al., "Crystal structure of unmodified tRNA$^{Gln}$ complexed with glutaminyl-tRNA synthetase and ATP suggests a possible role for pseudo-uridines in stabilization of RNA structure", Biochemistry, vol. 33, pp. 7560-7567, (1994).

Blake, R. C., II, et al., "Novel monoclonal antibodies with specificity for chelated uranium (VI): isolation and binding properties", Bioconjug. Chem. , vol. 15, pp. 1125-1136, (2004).

Boomer, D. W., et al, "Determination of uranium in environmental samples using inductively coupled plasma mass spectrometry", Anal. Chem., vol. 59, pp. 2810-2813, (1987).

Breaker, R. R., "Natural and engineered nucleic acids as tools to explore biology", Nature, vol. 432, pp. 838-845, (2004).

Brina, R. et al., "Direct detection of trace levels of uranium by laser-induced kinetic phosphorimetry", Anal Chem., vol. 64, pp. 1413-1418, (1992).

Chung N. et al., "Selective extraction of gold(III) in the presences of Pd(II) and Pt(IV) by saltin-out of the mixture of 2-propanol and water", Talanta, vol. 58, pp. 927-933, (2002).

Craft, E. et al., "Depleted and natural uranium: chemistry and toxicological effects", J. Toxicol. Environ. Health, Part B, vol. 7, pp. 297-317, (2004).

Demers, L. M. et al., "Thermal desorption behavior and binding properties of DNA bases and nucleosides on gold", J. Am. Chem. Soc. vol. 124, pp. 11248-11249, (2002).

Frankforter G. et al., "Equilibria in the systems of the higher alcohols, water and salts", J. Am. Chem. Soc., vol. 37, pp. 2697-2716 (1915).

Frankforter G., et al., "Equilibria in the systems, water, acetone and inorganic salts", J. Am. Chem. Soc., vol. 36, pp. 1103-1134, (1914).

Frankforter G., et al., "Equilibria in systems containing alcohols, salts and water, including a new method of alcohol analysis", J. Phys. Chem., vol. 17, pp. 402-473, (1913).

Ginnings, P. et al., "Ternary systems: water, tertiary butanol and salts at 30° C", J. Am. Chem. Soc., vol. 52, pp. 2282-2286, (1930).

Gongalsky, K., "Impact of pollution caused by uranium production on soil macrofauna", Environ. Monit. Assess., vol. 89, pp. 197-219, (2003).

Homola, J. et al., "Surface Plasmon Resonance (SPR) Sensors", Springer Series on Chemical Sensors and Biosensors, vol. 4, pp. 45-67, (2006).

US EPA, "Drinking water contaminants", found at http://www.epa.gov/safewater/contaminants/index.html, pp. 1-17, printed on Nov. 23, 2009.

Jones, L. A., et al., "Extraction of phenol and its metabolites from aqueous solution", J. Agric. Food Chem., vol. 41, pp. 735-741, (1993).

Katz, E. et al., "Integrated nanoparticle-biomolecule hybrid systems: sythesis, properties, and applications", Angew. Chem. Int. Ed., vol. 43, pp. 6042-6108, (2004).

Kobe, K. A. et al., "The ternary systems ethylene glycol-potassium carbonate-water and dioxane-potassium carbonate-water", J. Phys. Chem., vol. 446, p. 629-633, (1940).

Laromaine, A. et al., "Protease-triggered dispersion of nanoparticle assemblies", J. Am. Chem. Soc., vol. 129, pp. 4156-4157, (2007).

Lazarova, Z. et al., "Solvent extraction of lactic acid from aqueous solution", Journal of Biotechnology, vol. 32, pp. 75-82, (1994).

Lee, J. H. et al., "Site-specific control of distances between gold nanoparticles using phosphorothioate anchors on DNA and a short bifunctional molecular fastener", Angew. Chem. Int. Ed., vol. 46, pp. 9006-9010, (2007).

Leggett, D. C. et al., "Salting-out solvent extraction for preconcentration of neutral polar organic solutes from water", Anal. Chem., vol. 62, pp. 1355-1356, (1990).

Leinonen, H., "Stress corrosion cracking and life prediction evaluation of austenitic stainless steels in calcium chloride solution", Corrosion Science, vol. 52, No. 5, pp. 337-346, (1996).

Li, D. et al., "Amplified electrochemical detection of DNA through the aggregation of Au nanoparticles on elctrodes and the incorporation of methylene blue into the DNA-crosslinked structure", Chem. Comm., pp. 3544-3546, (2007).

Li, H. et al., "Detection of specific sequences in rna using differential adsorption of single-stranded oligonucleotides on gold nanoparticles", Anal. Chem., vol. 77 No. 19, pp. 6229-6233, (2005).

Li, H. et al., "Colorimetric detection of dna sequences based on electrostatic interactions with unmodified gold nanoparticles", Proc. Natl. Acad. Sci. U.S.A., vol. 101, pp. 14036-14039, (2004).

Li, H. et al., "Label-free colorimetric detection of specific sequences in genomic dna amplified by the polymerase chain reaction", J. Am. Chem. Soc., vol. 126, pp. 10958-10961, (2004).

Likidis, Z. et al., "Recovery of penicillin G from fermentation broth with reactive extraction in a mixer-settler", Biotechnology Letters, vol. 9, No. 4, pp. 229-232, (1987).

Lim, I. et al., "Homocysteine-mediated reactivity and assembly of gold nanoparticles", Langmuir, vol. 23, pp. 826-833, (2007).

Lu, Y. et al., "Functional DNA nanotechnology:emerging applications of DNAzymes and aptamers", Curr. Opion Biotech., vol. 17, pp. 580-588, (2006).

Long, F. A., et al., "Activity coefficients of nonelectrolyte solutes in aqueous salt solutions", Chem. Rev., vol. 51, pp. 119-169, (1952).

Lu, X. et al., "Salting-out separation and liquid-liquid equilibrium of tertiary butanol aqueous solution", Chemical Engineering Journal, vol. 78, pp. 165-171, (2000).

Lu, Y. et al., "Smart nanomaterials inspired by biology: dynamic assembly of error-free nanomaterials in response to multiple chemical and biological stimuli", Accounts of Chemical Research, vol. 40, pp. 315-323, (2007).

Mlakar, M. et al., "Stripping voltammetric determination of trace levels of uranium by synergic adsorptions", Analytica Chimica Acta, vol. 221, pp. 279-287, (1989).

Nishihama, S., "Review of advanced liquid-liquid extraction systems for the separation of metal ions by a combination of conversion of the metal species with chemical reaction", Ind. Eng. Chem. Res., vol. 40, pp. 3085-3091, (2001).

Pierotti, R. A., "A scaled particle theory of aqueous and nonaqueous solutions", Chemical Reviews, vol. 76, No. 6, pp. 717-726, (1976).

Centers for Disease Control, "Preventing lead poisoning in young children", U.S. Department of Health and Human Services, Public Health Service, Centers for Disease Control: Atlanta, GA, (1991).

Public Law 102-550; Residential Lead-Based Paint Hazard Reduction Act of the housing and Community Development Act of 1992; 28 pages, (1992).

Qiang, Z. et al., "Potentiometric determination of acid dissociation constants ($pK_a$) for human and veterinary antibiotics", Water Research, vol. 38, pp. 2874-2890, (2004).

Rohwer, H. et al., "Interactions of uranium and thorium with arsenazo III in an aqueous medium", Analytica Chimica Acta, vol. 341, pp. 263-268, (1997).

Safavi, A. et al., "A novel optical sensor for uranium determination", Analytica Chimica Acta vol. 530, pp. 55-60, (2005).

Sato, K. et al., "Rapid aggregation of gold nanoparticles induced by non-cross-linking DNA hybridization", J. Am. Chem. Soc., vol. 125, pp. 8102-8103, (2003).

Schenk, F. J. et. al., "Comparison of magnesium sulfate and sodium sulfate for removal of water from pesticide extracts of foods", J. AOAC International, vol. 85, No. 5, pp. 1177-1180, (2002).

Sessler, J. L. et al., "Hexaphyrin (1.0.1.0.0.0). A new colorimetric actinide sensor", Tetrahedron, vol. 60, pp. 11089-11097, (2004).

Shafer-Peltier, K. E. et al., "Toward a glucose biosensor based on surface-enhanced raman scattering", J. Am. Chem. Soc., vol. 125, pp. 588-593, (2003).

Sharma, J. et al., "DNA-templated self-assembly of two-dimensional and periodical gold nanoparticle arrays", Angew. Chem. Int. Ed., vol. 45, pp. 730-735, (2006).

Si, S. Et al., "pH-controlled reversible assembly of peptide-functionalized gold nanoparticles", Langmuir, vol. 23, pp. 190-195, (2007).

Simard, J. et al., "Formation and pH-controlled assembly of amphiphilic gold nanoparticles", Chemical Commun., pp. 1943-1944, (2000).

Singleton, V. L., "An extraction technique for recovery of flavors, pigments, and other constituents from wines and other aqueous solutions", Am. J. Enol. Vitic., vol. 12, pp. 1-8, (1961).

Rao, C.V.S.R. et al., "Extraction of acetonitrile from aqueous solutions. 1. Ternary liquid equilibria", Journal of Chemical and Engineering Data, vol. 23, No. 1, pp. 23-25, (1978).

Rao, D.S. et al., "Extraction of acetonitrile from aqueous solutions. 2. ternary liquid equilibria", Journal of Chemical and Engineering Data, vol. 24, No. 3, pp. 241-244, (1979).

Tabata, M. et al., "Ion-pair extraction of metalloporphyrins into acetonitrile for determination of copper(II)", Analytical Chemistry, vol. 68, no. 5, pp. 758-762, (1996).

Tabata, M. et al., "Chemical properties of water-miscible solvents separated by salting-out and their application To solvent extraction", Analytical sciences, vol. 10, pp. 383-388, (1994).

Van der Wal, Sj., "Low viscosity organic modifiers in reversed-phase HPLC", Chromatographia, vol. 20, No. 5, pp. 274-278, (1985).

Wang, J. et al., "A gold nanoparticle-based aptamer target binding readout for ATP assay", Adv. Mater., vol. 19, pp. 3943-3946, (2007).

Wang, L. et al., "Unmodified gold nanoparticles as a colorimetric probe for potassium DNA aptamers", Chem. Comm., vol. 36, 3780-3782, (2006).

Wang, Z. et al., "Label-free colorimetric detection of lead ions with a nanomolar detection limit and tunable dynamic range by using gold nanoparticles and DNAzyme", Advanced Materials, vol. 20, pp. 3263-3267. (2008).

Warren, K. W., Reduction of corrosion through improvements in desalting, Benelux Refinery Symposium, Lanaken, Belgium, 11 pages, (1995).

Wei, H. et al., "Simple and sensitive aptamer-based colorimetric sensing of protein using unmodified gold nanoparticle probes", Chem. Comm., vol. 36, pp. 3735-3737, (2007).

Wernette, D. P. et al., "Surface immobilization of catalytic beacons based on ratiometric fluorescent DNAzyme sensors: A systematic study", Langmuir, vol. 23, pp. 9513-9521, (2007).

Willner, I. et al., "Electronic aptamer-based sensors", Angew. Chem., Int. Ed., vol. 46, pp. 6408-6418, (2007).

Wu, Y. G., et al., "An extended Johnson-Furter equation to salting-out phase separation of aqueous solution of water-miscible organic solvents", Fluid Phase Equilibria, vol. 192, pp. 1-12, (2001).

Yan, H., "Nucleic acid nanotechnology", Science, vol. 306, pp. 2048-2049, (2004).

Yang, W. H. et al., "Discrete dipole approximation for calculating extinction and raman intensities for small particles with arbitrary shapes", J. Chem. Phys., vol. 103, pp. 869-875, (1995).

Deng, Z. et al., "DNA-Encoded self-assembly of gold nanoparticles into one-dimensional arrays", Angew. Chem Int. Ed., vol. 44, pp. 3582-3585, (2005).

Zhao, W. et al., "Simple and rapid colorimetric biosensors based on DNA aptamer and noncrosslinking gold naoparticle aggregation", ChemBioChem, vol. 8, pp. 727-731, (2007).

Zhao, W. et al., "Highly stabilized nucleotide-capped small gold nanoparticles with tunable size", Advanced Materials, vol. 19, pp. 1766-1771, (2007).

Zhao, W. et al., "DNA polymerization on gold nanoparticles through rolling circle amplification: towards novel scaffolds for three-dimensional periodic nanoassemblies", Angew. Chem. Int. Ed., vol. 45, pp. 2409-2413, (2006).

Zhao, W. et al., "DNA aptamer folding on gold nanoparticles: from colloid chemistry to biosensors", J. Am. Chem. Soc., vol. 130, (11), pp. 3610-3618, (2008).

Zhou, P. et al., "Extraction of oxidized and reduced forms of uranium from contaminated soils: effects of carbonate concentration pH", Environmental Science Technology, vol. 39, No. 12, pp. 4435-4440, (2005).

Jacoby, M., "Sensitive, selective mercury sensor nanoparticle-based colorimetric method detects part-per-billion levels of mercury", Chemical & Engineering News, pp. 1-3, May 2, 2007.

Cruz, R.P.G. et al., supplemental to "Dinucleotide junction cleavage versatility of 8-17 deoxyribozyme", Chemistry & Biology, vol. 11, pp. 57-67, (pp. 1-8) (2004).

Saleh, O. A. et al., "Direct detection of antibody-antigen binding using an on-chip artificial pore", Proceedings of The National Academy of Science, vol. 100, No. 3, pp. 820-824, (2003).

Han, C. et al., "Highly selective and sensitive colorimetric probes for $Yb^{3+}$ ions based on supramolecular aggregates assembled from B-cyclodextrin-4,4'-dipyridine inclusion complex modified silver nanoparticles", Chem. Commun., pp. 3545-3547, (2009).

Aldaye, F.A., et al., "Sequential Self-Assembly of a DNA Hexagon as a Template for the Organization of Gold Nanoparticles", Angew. Chem. Int. Ed., 45, pp. 2204-2209, (2006).

Loweth, C.J. et al., "DNA-Based Assembly of Gold Nanocrystals", Angew. Chem. Int. Ed., 38, No. 12, pp. 1808-1812, (1999).

Carbone, A., et al., "Circuits and programmable self-assembling DNA structures", Proceedings of the National Academy of Sciences of the United States of America, vol. 99, No. 20, pp. 12577-12582, (2002).

Chelyapov, N., et al., "DNA Triangles and Self-Assembled Hexagonal Tilings", J. Am. Chem. Soc., 126, pp. 13924-13925, (2004).

Conway, N.E., et al., "The Covalent Attachment of Multiple Fluorophores to DNA Containing Phosphorothioate Diesters Results in Highly Sensitive Detection of Single-Stranded DNA", Bioconjugate Chem, 2, pp. 452-457, (1991).

Ding, B., et al., "Pseudohexagonal 2D DNA Crystals from Double Crossover Cohesion", J. Am. Chem. Soc., 126, pp. 10230-10231, (2004).

Endo, M., et al., "DNA Tube Structures Controlled by a Four-Way-Branched DNA Connector", Angew. Chem. Int. Ed., 44, pp. 6074-6077, (2005).

Fidanza, J.A, et al. "Site-Specific Labeling of DNA Sequences Containing Phosphorothioate Diesters", J. Am. Chem. Soc., 114, pp. 5509-5517, (1992).

Goodman, R.P., et al., "Rapid Chiral Assembly of Rigid DNA Building Blocks for Molecular Nanofabrication", Science, 310, pp. 1661-1665, (2005).

Hagleitner, C., et al., "Smart single-chip gas sensor microsystem", Nature, vol. 414, pp. 293-296, (2001).

He, Y., et al., "Sequence Symmetry as a Tool for Designing DNA Nanostructures", Angew. Chem. Int. Ed., 44, pp. 6694-6696, (2005).

Heath, J.R., et al., "A Defect-Tolerant Computer Architecture: Opportunities for Nanotechnology", Science, vol. 280, pp. 1716-1719, (1998).

Holloway, G., et al., "An Organometallic Route to Oligonucleotides Containing Phosphoroselenoate", ChemBioChem, 3, pp. 1061-1065, (2002).

Li, H., et al., "DNA-Templated Self-Assembly of Protein and Nanoparticle Linear Arrays", J. Am. Chem. Soc., 126, pp. 418-419, (2004).

Cunningham, L., et al., "Spectroscopic Evidence for Inner-Sphere Coordination of Metal Ions to the Active Site of a Hammerhead Ribozyme", J. Am. Chem. Soc., 120, pp. 4518-4519, (1998).

Luduena, R.F., et al., N,N-Bis($\alpha$-iodoacetyl)-2,2'-dithiobis(ethylamine), a Reversible Crosslinking Reagent for Protein Sulfhydryl Groups, Analytical Biochemistry, 117. pp. 76-80, (1981).

Lund, K., et al., "Self-Assembling a Molecular Pegboard", J. Am. Chem. Soc., 127, pp. 17606-17607, (2005).

Mathieu, F., et al. "Six-Helix Bundles Designed from DNA", Nano Letters, vol. 5, No. 4, pp. 661-665, (2005).

Liu, H., et al, "Approaching the Limit: Can One DNA Oligonucleotide Assemble into Large Nanostructures?", Angew. Chem., 118, pp. 1976-1979, (2006).

Fidanza, J. et al, "Introduction of Reporter Groups at Specific Sites in DNA Containing Phosphorothioate Diesters", J. Am. Chem. Soc., 111, pp. 9117-9119, (1989).

Nakao, H., et al, "Highly Ordered Assemblies of Au Nanoparticles Organized on DNA", Nano Letters, vol. 3, No. 10, pp. 1391-1394, (2003).

Patolsky, F., et al., "Au-Nanoparticle Nanowires Based on DNA and Polylysine Templates", Angew. Chem. Int. Ed., 41, No. 13, pp. 2323-2327, (2002).

Pinto, Y., et al., "Sequence-Encoded Self-Assembly of Multiple-Nanocomponent Arrays by 2D DNA Scaffolding", Nano Letters, vol. 5, No. 12, pp. 2399-2402, (2005).

Rothemund, P., "Folding DNA to create nanoscale shapes and patterns", Nature, vol. 440, pp. 297-302, (2006).

Yang, X., et al, "Ligation of DNA Triangles Containing Double Crossover Molecules", J. Am. Chem. Soc., 120, pp. 9779-9786, (1998).

Seeman, N.C., "Nucleic Acid Nanostructures and Topology", Angew. Chem. Int. Ed., 37, pp. 3220-3238, (1998).

Seeman, N. C., "At the Crossroads of Chemistry, Biology, and Materials: Structural DNA Nanotechnology", Chemistry & Biology, vol. 10, pp. 1151-1159, (2003).

Le, J.D., et al., "DNA—Templated Self-Assembly of Metallic Nanocomponent Arrays on a Surface", Nano Letters, vol. 4, No. 12, pp. 2343-2347, (2004).

Seeman, N.C., et al. "Nucleic acid nanostructures: bottom-up control of geometry on the nanoscale", Reports on Progress in Physics, 68, pp. 237-270, (2005).

Warner, M.G., et al., "Linear assemblies of nanoparticles electrostatically organized on DNA scaffolds", Nature Materials, vol. 2, pp. 272-277, (2003).

Winfree, E., et al., "Design and self-assembly of two-dimensional DNA crystals", Nature, vol. 394, pp. 539-544, (1998).

Woehrle, G.H., et al., "Molecular-Level Control of Feature Separation in One-Dimensional Nanostructure Assemblies Formed by Biomolecular Nanolithography", Langmuir, 20, pp. 5982-5988, (2004).

Zhang, J., et al, "Periodic Square-Like Gold Nanoparticle Arrays Templated by Self-Assembled 2D DNA Nanogrids on a Surface", Nano Letters, vol. 6, No. 2, pp. 248-251, (2006).

Yang, T. et al. "Tunneling Phase Logic Cellular Nonlinear Networks", International Journal of Bifurcation and Chaos, vol. 11, No. 12, pp. 2895-2911, (2001).

Liu, Z., et al., "Imaging DNA Molecules on Mica Surface by Atomic Force Microscopy in Air and in Liquid", Microscopy Research and Technique, 66, pp. 179-185, (2005).

Niemeyer, C.M., et al., "Covalent DNA-Streptavidin Conjugates as Building Blocks for Novel Biometallic Nanostructures", Angew. Chem. Int. Ed., 37, No. 16, pp. 2265-2268, (1998).

"What wavelength goes with a color" from eosweb. larc. Nasa.gov. Printed on Jan. 7, 2011.

Cadmium sulfide from Wikipedia, the free encyclopedia. Printed on Jan. 7, 2011.

Yeh et al., Quantum dot-mediated biosensing assays for specific nucleic acid detection. Nanomedicine, 1, 115-121, 2005.

* cited by examiner

SEQUENCE LISTING

```
<160> NUMBER OF SEQ ID NOS: 5

<210> SEQ ID NO 1
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 1
tcatgtttgt tgttggccc ccttctttc tta                                    33

<210> SEQ ID NO 2
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
acaaacatga                                                             10

<210> SEQ ID NO 3
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
```

-continued

```
<400> SEQUENCE: 3
tcatgtttct tctgttgccc ccttctgttg tat                                  33

<210> SEQ ID NO 4
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tcatgtttct tctgttgccc ccttctgttg ttt                                  33

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
tcatgtttct tctgttgggg gcttctgttg ttt                                  33
```

US 8,062,893 B2

FLUORESCENT SENSOR FOR MERCURY

CROSS REFERENCE TO RELATED APPLICATION

This application claims priority to provisional application No. 61/104,555 entitled "Fluorescent Sensor For Mercury" filed 10 Oct. 2008, the entire contents of which are hereby incorporated by reference, except where inconsistent with the present application.

FEDERALLY SPONSORED RESEARCH OR DEVELOPMENT

The subject matter of this application may have been funded in part by the National Science Foundation (DMI-0328162, DMR-0117792, and CTS-0120978), and the U.S. Department of Energy (DE-FG02-01ER63173). The federal government may have certain rights in this invention.

SEQUENCE LISTING

The instant application contains a Sequence Listing which has been submitted via EFS-Web and is hereby incorporated by reference in its entirety. Said ASCII copy, created on Nov. 20, 2009, is named ILL10-133-US_SEQUENCE_LISTING, and is 1,460 bytes in size.

BACKGROUND

Mercury is a highly toxic and widespread pollutant in the environment. Mercury can be a source of environmental contamination when present in by-products of burning coal, mine tailings and wastes from chlorine-alkali industries.[1,2] These contaminations can cause a number of severe health effects such as brain damage, kidney failure, and various cognitive and motion disorders.[3] Therefore, there is high demand for sensitive and selective mercury detection.

Towards this goal, many mercury sensors based on small fluorescent organic molecules,[4-11] conjugated polymers,[12] foldamers,[13,14] genetically engineered cells,[15] proteins,[16-18] oligonucleotides,[19,20] membranes,[21,22] electrodes,[23,24] and nanomaterials[25-30] have been reported. Despite this progress, few sensors show enough sensitivity and selectivity for detection of mercury in aqueous solutions.

Sensors that meet such requirements remain complicated to design and operate, or are vulnerable to interference, making difficult facile on-site and real-time detection and quantification of mercury. A particular interesting example is environmental-monitoring applications, such as mercury detection in drinking water, in which a detection limit below 10 nM (the maximum contamination level, as defined by the U.S. Environmental Protection Agency (EPA)) is required. However, only a few reported sensors can reach this sensitivity.[11,15,18,26,27] Therefore, a simple sensor with high sensitivity and selectivity for facile on-site and real-time mercury detection is still needed.

Polynucleotides provide an attractive methodology for mercury sensing. Ono and co-workers reported that mercury ion $Hg^{2+}$ has the unique property of binding specifically to two thymine bases and stabilize thymine-thymine mismatches in a DNA duplex; they demonstrated a fluorescent sensor for $Hg^{2+}$ ion detection based on this property.[19,31] In their sensor design, one single-stranded thymine-rich polynucleotide was labeled with a fluorophore and quencher at each end. In the presence of $Hg^{2+}$ ions, the two ends of the polynucleotide became closer to each other through thymine-Hg-thymine base pair formation, resulting in fluorescence decrease due to an enhanced quenching effect between the fluorophore and quencher. A detection limit of 40 nM was reported.

The $Hg^{2+}$ ion-induced stabilization effect on thymine-thymine mismatches has also been used to design colorimetric sensors with DNA and gold nanoparticles based on labeled[25,29] or label free methods.[27,28,30] Recently, Liu et al. reported a highly sensitive mercury sensor based on a uranium-specific DNAzyme by introducing thymine-thymine mismatches in the stem region of the original DNAzyme.[32] $Hg^{2+}$ enhanced the DNAzyme activity through allosteric interactions, and a detection limit as low as 2.4 nM was achieved.

Although highly sensitive and selective, this sensor however requires the use of 1 μM $UO_2^{2+}$ for DNAzyme activity. This drawback creates the motivation to find an alternative method for mercury sensing, with comparable sensitivity but without the need to use other toxic metal ions as co-factors.

Fluorescent sensors based on structural switching aptamers have been developed to detect a number of non-metal ions such as adenosine-5'-triphosphate (ATP),[33-35] cocaine,[36] thrombin,[37] and platelet-derived growth factor (PDGF).[38] Aptamers switch structure in the presence of an effector usually due to the formation of non-covalent interactions, such as hydrogen bonds, ionic bonds and Van der Waals interactions, between the aptamer binding site and the effector.

SUMMARY

In a first aspect, the present invention provides a sensor for detecting mercury, comprising: a first polynucleotide, comprising a first region, and a second region, a second polynucleotide, a third polynucleotide, a fluorophore, and a quencher, wherein the third polynucleotide is optionally linked to the second region; the fluorophore is linked to the first polynucleotide and the quencher is linked to the second polynucleotide, or the fluorophore is linked to the second polynucleotide and the quencher is linked to the first polynucleotide; the first region and the second region hybridize to the second polynucleotide; and the second region binds to the third polynucleotide in the presence of $Hg^{2+}$ ions.

In a second aspect, the present invention provides a method of detecting the presence of mercury in a sample, comprising: (a) forming a mixture comprising the sample and a sensor comprising: a first polynucleotide, comprising a first region, and a second region, a second polynucleotide, a third polynucleotide, a fluorophore, and a quencher, wherein the third polynucleotide is optionally linked to the second region; the fluorophore is linked to the first polynucleotide and the quencher is linked to the second polynucleotide, or the fluorophore is linked to the second polynucleotide and the quencher is linked to the first polynucleotide; the first region and the second region hybridize to the second polynucleotide; and the second region binds to the third polynucleotide in the presence of $Hg^{2+}$ ions, and (b) measuring the fluorescence of the mixture.

In a third aspect, the present invention provides a method of determining the concentration of mercury in a sample, comprising: (a) forming a mixture comprising the sample and a sensor comprising: a first polynucleotide, comprising a first region, and a second region, a second polynucleotide, a third polynucleotide, a fluorophore, and a quencher, wherein the third polynucleotide is optionally linked to the second region; the fluorophore is linked to the first polynucleotide and the quencher is linked to the second polynucleotide, or the fluorophore is linked to the second polynucleotide and the quencher is linked to the first polynucleotide; the first region and the second region hybridize to the second polynucleotide; and the second region binds to the third polynucleotide in the presence of $Hg^{2+}$ ions, (b) measuring the fluorescence of the mixture; and (c) comparing the measurement obtained in (b) with that of a calibration curve created using known concentrations of mercury.

DEFINITIONS

Figure 1:
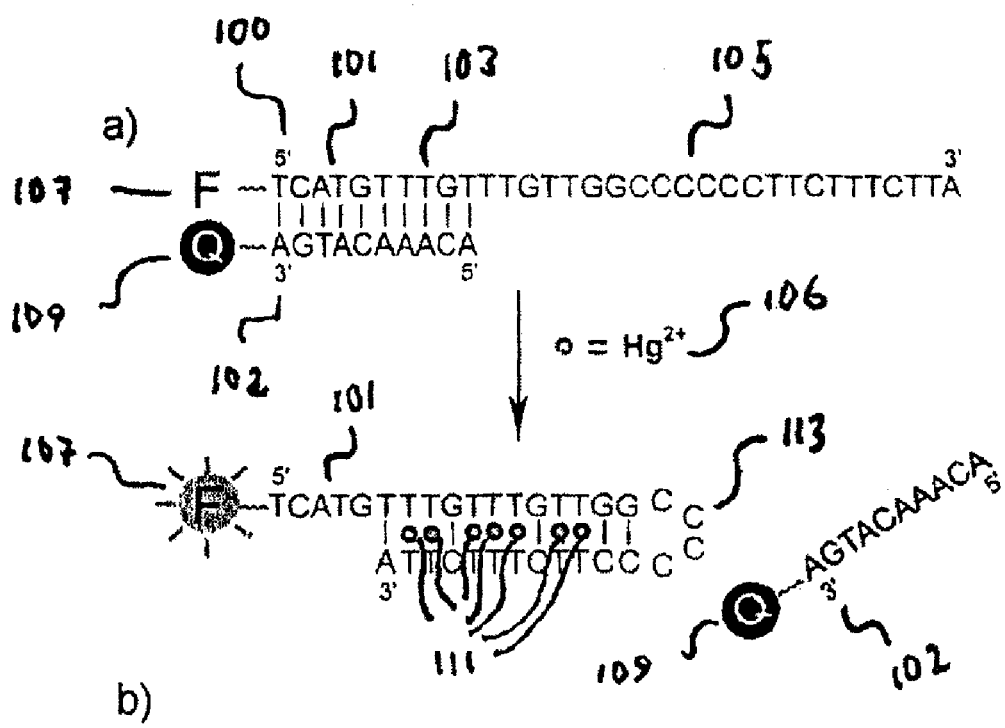
FIG. 1(a) illustrates the structure of an example fluorescent mercury sensor according to the invention (SEQ ID NOS 1, 2, 1 and 2, respectively, in order of appearance).
FIG. 1(b) illustrates the fluorescence spectra of the sensor in the absence of, and after the addition of, 1 μM $Hg^{2+}$ ions for 10 minutes.
Figure 1:
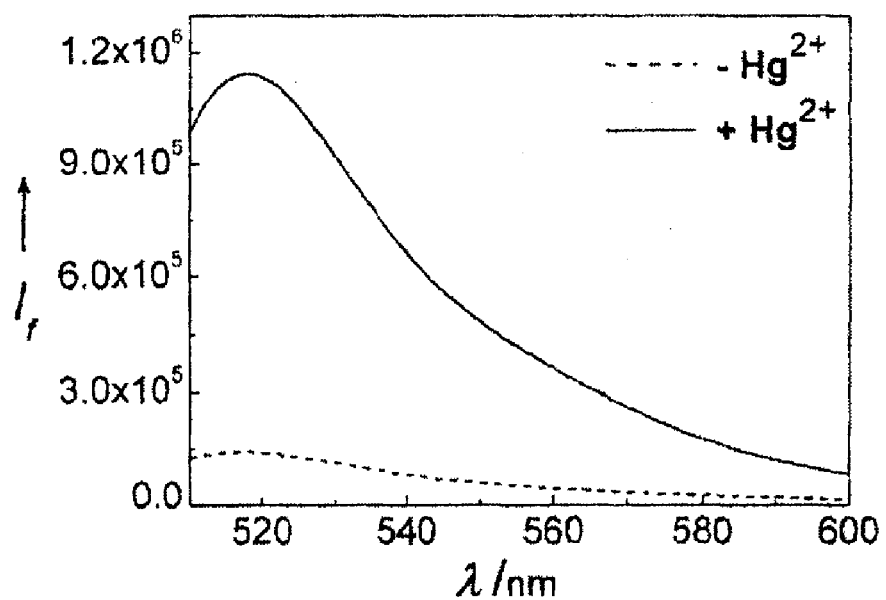

"Thymine-Hg-thymine base pair" refers to a coordination complex formed by the binding of two thymines to a mercury ion $Hg^{2+}$.

"Thymine-thymine mismatch" refers to two thymines that form a thymine-Hg-thymine base pair in the presence of $Hg^{2+}$.

"Polynucleotide" refers to a nucleic acid sequence having at least two nucleotides. Polynucleotides may contain naturally-occurring nucleotides and synthetic nucleotides. DNA, RNA and PNA molecules are embraced by this term.

"Sensitivity" refers to the smallest increase of an analyte concentration that can be detected by the sensor.

"Detection limit" refers to the limits of detection of an analytical device.

"Base-pairing" or "hybridization" refers to the ability of a polynucleotide to form at least one hydrogen bond with a nucleotide under low stringency conditions. The nucleotide may be part of a second polynucleotide or a nucleotide found within the first polynucleotide. A polynucleotide is at least partially complementary to a second polynucleotide when the first polynucleotide is capable of forming at least one hydrogen bond with the second polynucleotide. To be partially complementary, a polynucleotide may have regions wherein base pairs may not form surrounded by those regions that do, forming loops, stem-loops, and other secondary structures.

DETAILED DESCRIPTION

The present invention provides a simple design of a highly sensitive and selective fluorescent mercury ion $Hg^{2+}$ sensor based on structure-switching polynucleotides. The sensing process can be completed in less than 5 minutes, with a detection limit of 3.2 nM (0.6 ppb) and a detection range of 3 nM to 800 nM.

In contrast to fluorescent sensors based on aptamers developed in the past, the sensor of the present invention is based on the structure-switching of polynucleotides that is induced by the binding of two thymines to the mercury ion $Hg^{2+}$, forming thymine-Hg-thymine base pairs. The analyte $Hg^{2+}$ is therefore bound through a thymine-Hg-thymine base pair, as opposed to the ionic, hydrogen-bonding, and Van der Waals forces that usually bind analytes to aptamers and DNAzymes.

FIG. 1(a) illustrates an example sensor according to the invention. To detect the target $Hg^{2+}$, a sample suspected of containing $Hg^{2+}$ is mixed with a first polynucleotide 100 and a second polynucleotide 102 together in a solution of appropriate ionic strength. The first polynucleotide 100 has a fluorophore F 107 linked at the 5' end, and the second polynucleotide 102 has a quencher Q 109 linked at the 3' end. Polynucleotide 100 can be divided in two regions. The first region 101 together with the second region 103 hybridizes with polynucleotide 102. A third polynucleotide 105 may be linked to the second region 103 or be a separate polynucleotide. In the example of FIG. 1(a), the second region and the third polynucleotide are linked. In the absence of mercury ions $Hg^{2+}$, as polynucleotides 100 and 102 are hybridized, the fluorophore and quencher are in close proximity to each other, resulting in fluorescence quenching due to fluorescence resonance energy transfer. In the presence of mercury ions $Hg^{2+}$ 106, the formation of thymine-Hg-thymine base pairs 111 will induce the binding of the second region with the third polynucleotide. In the example of FIG. 1(a), the formation of thymine-Hg-thymine base pairs will induce the folding of the second region and the third polynucleotide into a hairpin structure 113. As a result, only the first region 101 will remain hybridized to the second polynucleotide 102, which is not sufficient to hold the two polynucleotides together at the ionic strength and temperature of the mixture. Therefore, the second polynucleotide will be released from first polynucleotide, resulting in signal from the fluorophore.

Each part is now described in further detail.

As the binding of the second region and third polynucleotide is driven by the formation of thymine-Hg-thymine base pairs between thymines and $Hg^{2+}$, the second region and the third polynucleotide should form a sufficient number of thymine-thymine mismatches to induce binding under the conditions in which the sensor is employed, such as ionic strength, pH, and temperature. Preferably, the second region and the third polynucleotide form 2 to 20 thymine-thymine mismatches. More preferably, the second region and the third polynucleotide form 4 to 10 thymine-thymine mismatches. Most preferably, the second region and the third polynucleotide form 5 to 8 thymine-thymine mismatches. In addition, the second region may include bases complementary to bases of the third polynucleotide.

The first polynucleotide preferably comprises a total of 10 to 100 nucleotides. More preferably, the first polynucleotide comprises 25 to 40 nucleotides. Most preferably, the first polynucleotide comprises 30 to 35 nucleotides.

Essentially any fluorophore may be used, including BODIPY, TAMRA, fluoroscein, fluoroscein substitutes (Alexa Fluor dye, Oregon green dye), long wavelength dyes, and UV-excited fluorophores. These and additional fluorphores are listed in Fluorescent and Luminescent Probes for Biological Activity. A Practical Guide to Technology for Quantitative Real-Time Analysis, Second Ed. W. T. Mason, ed. Academic Press (1999) (incorporated herein by reference). In preferred embodiments, the fluorophore is FAM.

Quenchers may be categorized as non-fluorescent and fluorescent quenchers. Non-fluorescent quenchers are capable of quenching the fluorescence of a wide variety of fluorophores. Usually, non-fluorescent quenchers absorb energy from the fluorophore and release the energy as heat. Examples of non-fluorescent quenchers include DABCYL, QSY-7, and QSY-33. Preferred non-fluorescent quenchers include Black Hole Quenchers (BHQs).

Fluorescent quenchers tend to be specific to fluorophores that emit at a specific wavelength range. Fluorescent quenchers often involve fluorescence resonance energy transfer (FRET). In many instances the quencher is also a fluorophore. In such cases, close proximity of the fluorophore and quencher is indicated by a decrease in fluorescence of the fluorophore and an increase in fluorescence in the fluorescent quencher. Commonly used fluorophore/fluorescent quencher pairs include fluorescein/tetramethylrhodamine, IAEDANS/fluorescein, fluorescein/fluorescein, and BODIPY FL/BODIPY FL.

The fluorophore could be linked essentially anywhere on the first polynucleotide and the quencher essentially anywhere on the second polynucleotide, as long as they are in close proximity to each other when the two polynucleotides are hybridized. By close proximity, it is meant that they are situated such that the quencher is able to function. Furthermore, the quencher may be placed on the first polynucleotide and the fluorophore on the second polynucleotide. Dehybridization removes the fluorophore from the quencher, leading to an increase in fluorescence.

It is preferred to have the fluorophore linked to the 5' end of the first polynucleotide and the quencher linked to the 3' end of the second polynucleotide such that when the polynucleotides are hybridized, the fluorophore and the quencher are in close proximity to each other. Alternatively, the fluorophore may be linked to the 3' end of the second polynucleotide and the quencher linked to the 5' end of the first polynucleotide.

When choosing a fluorophore, quencher, or where to position the molecules, it is important to consider, and preferably to test, the effect of the fluorophore or quencher on the hybridization of the first polynucleotide and second polynucleotide and on the binding between the second region and the third polynucleotide. Also, it is preferable that the fluorophore display a high quantum yield and energy transfer efficiency. Long-wavelength (excitation and emission) fluorophores are preferred because of less interference from other absorbing species. The fluorophore should also be less sensitive to pH changes or to non-specific quenching by metal ions or other species.

Sometimes other factors in a solution such as pH, salt concentration or ionic strength, or viscosity will have an effect on fluorescence. Others may affect the hybridization of the first polynucleotide and second polynucleotide. Therefore, in preferred methods, controls are run to determine if the solution itself, regardless of the hybridization, is altering the fluorescence. Such controls include the use of a first polynucleotide and third polynucleotide that do not dehybridize or the first polynucleotide without the presence of the third polynucleotide.

The invention also provides methods for detecting the presence of $Hg^{2+}$ in samples suspected of containing the ion. In certain embodiments, a mixture of the sample and the sensor of the invention is formed, and the resulting fluorescence, if any, is measured. For example, the sample and sensor can be mixed in a cuvette and fluorescent readings taken in a fluorimeter.

However, essentially any instrument or method for detecting fluorescent emissions may be used. Furthermore, the fluorescence may be measured by a number of different modes. Examples include fluorescence intensity, lifetime, and anisotropy in either steady state or kinetic rate change modes.[39]

The sample is preferably liquid. More preferably, the sample is aqueous, for example industrial discharge, lake-, river-, or pond-water, and especially drinking water. Biological and bodily fluids such as plasma and blood are also contemplated. Solid and gaseous samples, for instance industrial waste or emissions, can also be analyzed for mercury presence, for example following a pretreatment process that includes dispersion or solubilization in a suitable liquid medium. Food, for example fish, meat, and milk, may also be analyzed for the presence of $Hg^{2+}$. Preferably other ions, especially other metal ions, may be present in the sample. However, no other ions, such as co-factors, need be present for detection.

The invention also provides methods for determining the concentration of $Hg^{2+}$ in a sample. A calibration curve is first taken with known concentrations of $Hg^{2+}$. The fluorescent reading of the sample to be analyzed is scored against the curve, thereby yielding the $Hg^{2+}$ concentration in the sample.

Also provided are sensor system kits for detecting $Hg^{2+}$. In one embodiment, the kit includes at least a first container. The first container contains the sensor.

When a kit is supplied, the different components of the sensor may be packaged in separate containers and admixed immediately before use. Such packaging of the components separately permits long-term storage of the active components.

The reagents included in the kits can be supplied in containers of any sort such that the life of the different components are preserved and are not adsorbed or altered by the materials of the container. For example, sealed glass ampules may contain one of more of the reagents, or buffers that have been packaged under a neutral, non-reacting gas, such as nitrogen. Ampules may consist of any suitable material, such as glass, organic polymers, such as polycarbonate, polystyrene, etc.; ceramic, metal or any other material typically employed to hold similar reagents. Other examples of suitable containers include simple bottles that may be fabricated from similar substances as ampules; and envelopes that may comprise foil-lined interiors, such as aluminum or an alloy. Other containers include test tubes, vials, flasks, bottles, syringes, or the like. Containers may have a sterile access port, such as a bottle having a stopper that can be pierced by a hypodermic injection needle. Other containers may have two compartments that are separated by a readily removable membrane that upon removal permits the components to be mixed. Removable membranes may be glass, plastic, rubber, etc.

The kits may also contain other reagents and items useful for detecting $Hg^{2+}$. The reagents may include standard solutions containing known quantities of $Hg^{2+}$, dilution and other buffers, pretreatment reagents, etc. Other items which may be provided include syringes, pipettes, cuvettes and containers. Standard charts indicating the fluorescence of the sensor, corresponding to the presence of different amounts of $Hg^{2+}$ in the sample being tested, may be provided.

Kits may also be supplied with instructional materials. Instructions may be printed on paper or other substrate, and/or may be supplied as an electronic-readable medium, such as a floppy disc, CD-ROM, DVD-ROM, Zip disc, videotape, audiotape, etc. Detailed instructions may not be physically associated with the kit; instead, a user may be directed to an internet web site specified by the manufacturer or distributor of the kit, or supplied as electronic mail.

EXAMPLE

Example 1

Fluorimetric $Hg^{2+}$ Sensor

The design of a structure-switching sensor for $Hg^{2+}$ is shown in FIG. 1. It is based on a first polynucleotide and a second polynucleotide. The first polynucleotide had 33 bases and was labeled with a FAM fluorophore at the 5' end. The second polynucleotide had 10 bases and was labeled with a Black Hole Quencher-1 at the 3' end (FIG. 1(a)). The first polynucleotide comprised 5 self-complementary base pairs and seven thymine-thymine mismatches. The fluorescence spectra of the sensor before and after the addition of 1 µM $Hg^{2+}$ is shown in FIG. 1(b). An approximately eight-fold fluorescence increase at the 518 nm peak was observed. The quantum yield of the FAM linked to the first polynucleotide was estimated to be ~66% and little quenching of FAM fluorescence was observed upon addition of 1 µM $Hg^{2+}$.

Figure 2:
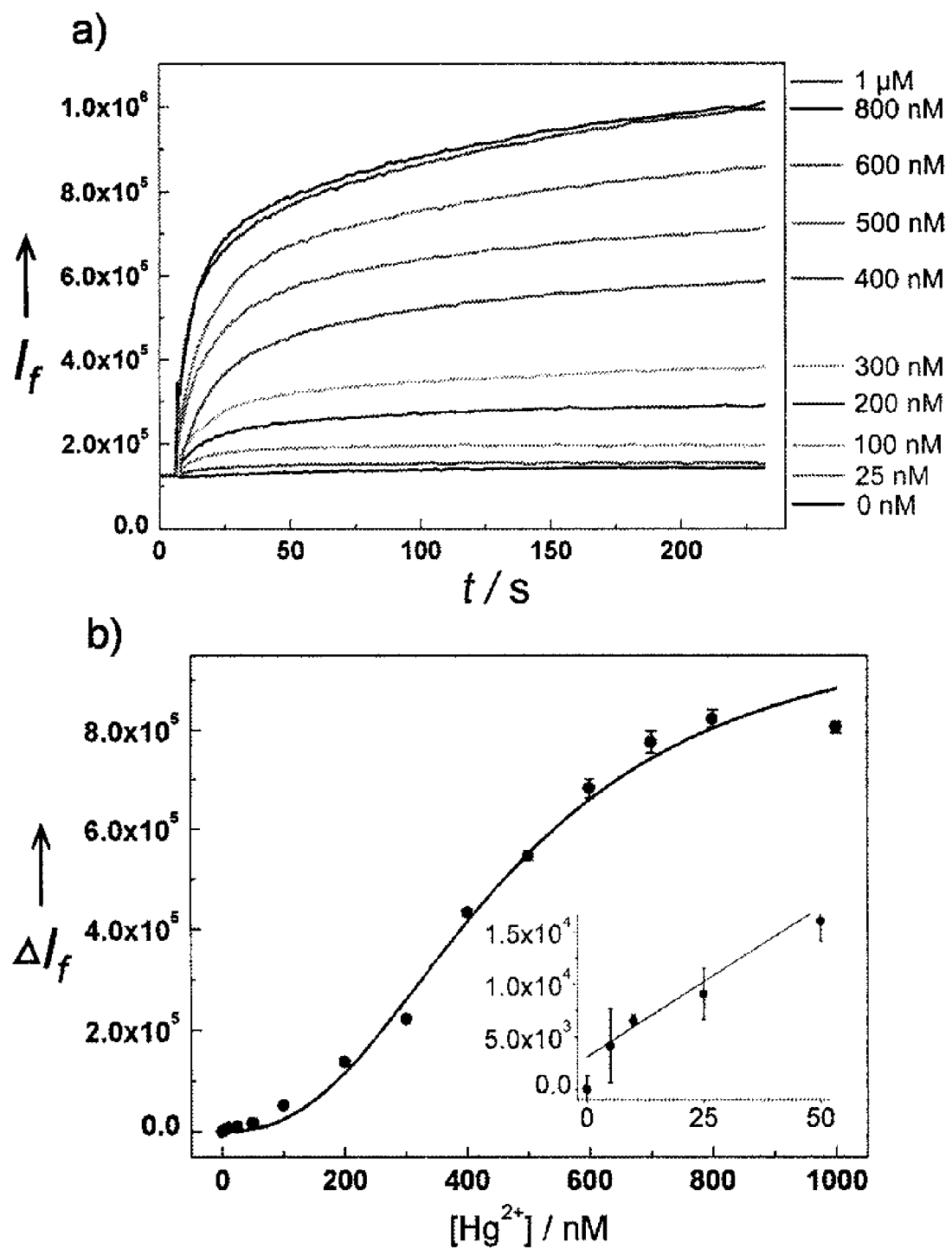
FIG. 2(a) illustrates the kinetics of the fluorescence increase in the presence of varying concentrations of $Hg^{2+}$.
FIG. 2(b) illustrates a calibration curve of the fluorescent mercury sensor. The inset illustrates the sensor responses at low $Hg^{2+}$ concentrations.

To study the $Hg^{2+}$ induced structure-switching of the sensor system, sample solutions were treated with $Hg^{2+}$ ions in various conditions, and the kinetics of the fluorescence increase at 518 nm was monitored. As shown in FIG. 2(a), higher concentrations of $Hg^{2+}$ ions resulted in higher fluorescence emission enhancement. To quantify the $Hg^{2+}$ ions, the fluorescence increase in the first three minutes after addition of different concentrations of $Hg^{2+}$ ions was collected and compared. The calibration curve (FIG. 2(b)) had a sigmoid shape and was fit to a Hill plot with a Hill coefficient of 2.4. These results indicate that the $Hg^{2+}$ binding to the first polynucleotide is a positively cooperative process, and the binding of one $Hg^{2+}$ facilitates the binding of another $Hg^{2+}$ onto the same polynucleotide. Although there were seven binding sites in the first polynucleotide, the release of the second polynucleotide occurred after binding to approximately 2.4 $Hg^{2+}$ ions. By fitting the calibration curve of FIG. 2(b) to a Hill plot, a dissociation constant of 471 nM was obtained. This sensor had a detection limit of 3.2 nM based on the 3α/slope, which is lower than the toxic level of $Hg^{2+}$ in drinking water as defined by the U.S. EPA. The calibration saturated at 800 nM, meaning that the detection range of this sensor is from 3 nM to 800 nM.

Figure 3:
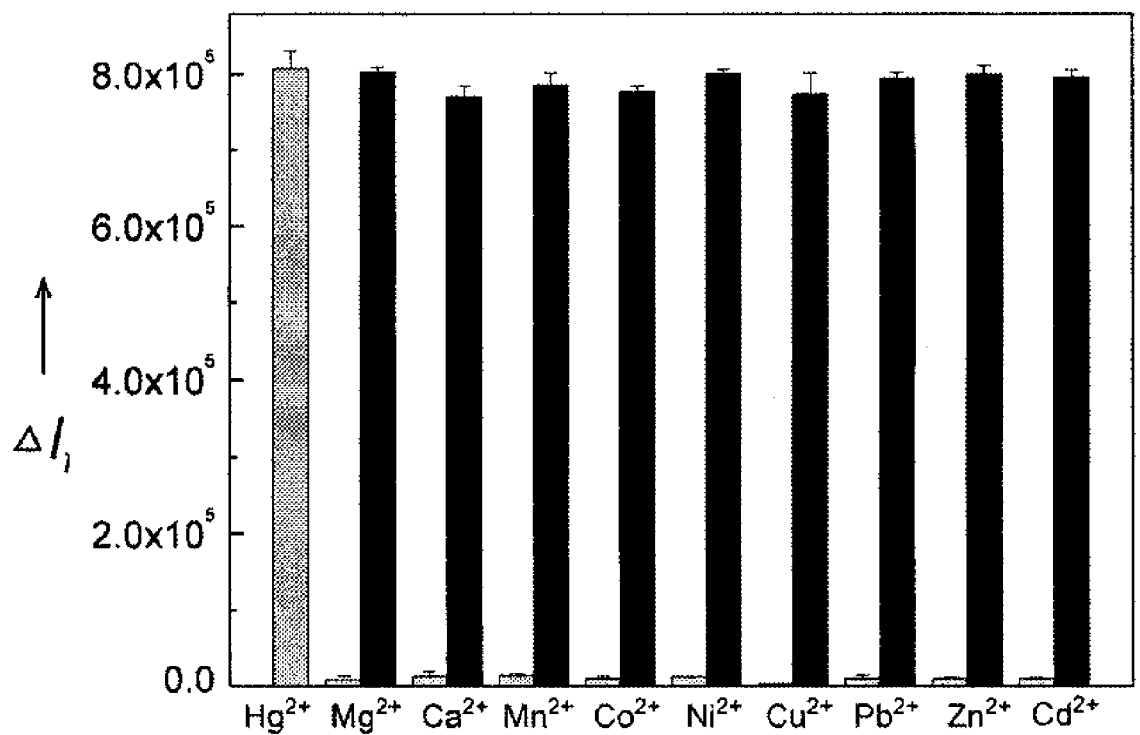
FIG. 3 illustrates the selectivity of the mercury sensor. Gray bars represent fluorescent responses 8 minutes after addition of 1 μM of a number of metal ions. Black bars represent fluorescent responses after addition of 1 μM of $Hg^{2+}$ together with 1 μM of a metal ion other than $Hg^{2+}$.

To determine the selectivity of the sensor, 1 µM of each of a number of metal ions was added individually to the sensor solution, and the fluorescence increase was monitored. As shown by they gray bars in FIG. 3, among the metal ions tested ($Mg^{2+}$, $Ca^{2+}$, $Mn^{2+}$, $Co^{2+}$, $Ni^{2+}$, $Cu^{2+}$, $Pb^{2+}$, $Zn^{2+}$, $Cd^{2+}$, and $Hg^{2+}$), only $Hg^{2+}$ yielded a significant increase in fluorescence. In addition, 1 µM of $Hg^{2+}$ and 1 µM of each of the other tested metal ions were added together to the sensor solution. The fluorescence response (FIG. 3, black bars) shows excellent selectivity for $Hg^{2+}$ over other metal ions.

Figure 4:
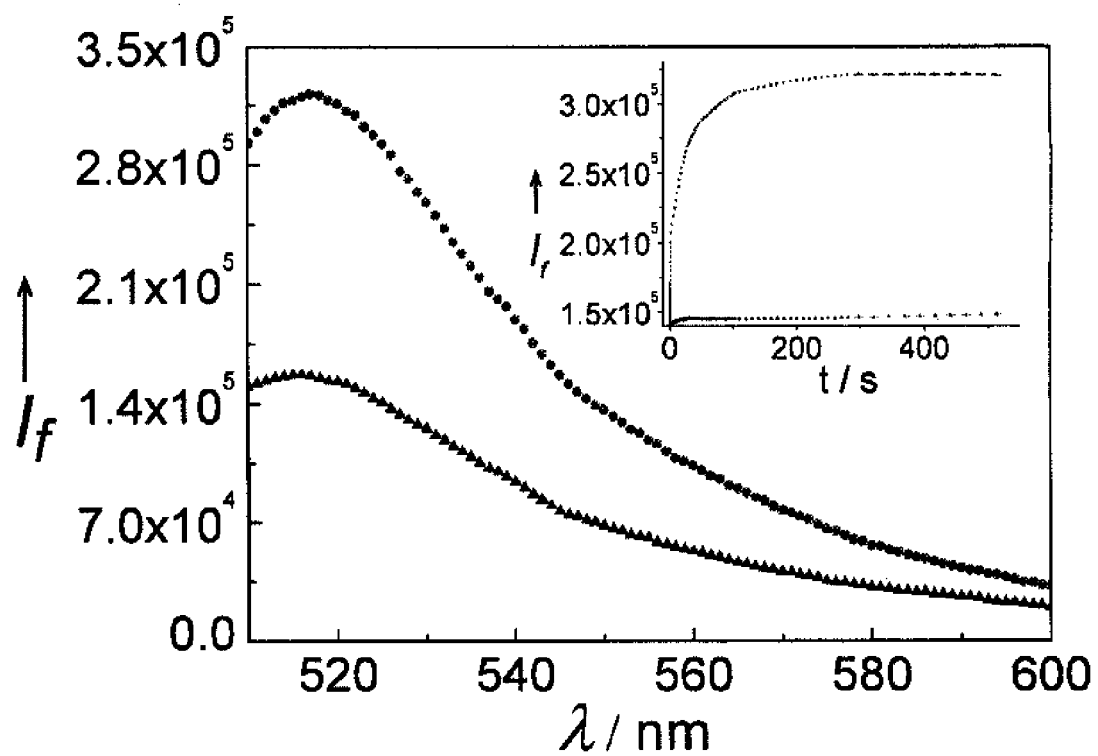
FIG. 4 illustrates fluorescence spectra corresponding to the analysis of pond water containing no $Hg^{2+}$ (triangles) or 500 nM $Hg^{2+}$ (circles). The inset illustrates the kinetics of the fluorescence increase after the addition of the pond water.

The sensor was further tested with pond water collected on the University of Illinois (Urbana-Champaign, Ill.) campus. The pond water with standard addition of $Hg^{2+}$ ions was added to the sensor solution with a dilution factor of 2.8, and the fluorescence change was monitored. Following standard addition methods, $Hg^{2+}$ ions were added to the pond water to a final concentration of 200 nM, and a 207% increase in fluorescence was observed (FIG. 4). This result is similar to the 231% fluorescence increase observed with the sensor for pure water in the presence of 200 nM $Hg^{2+}$. These results indicate that the sensor is able to detect mercury in pond water with little interference.

Experimental

Sensor Preparation and Mercury Detection

All polynucleotides were purchased from Integrated DNA Technologies (Coralville, Iowa) and were purified by HPLC. To prepare the sensor solution, 100 nM Strand A (5'-FAM-TCATGTTTGTTTGTTGGCCCCCCTTCTTTCTTA-3') (SEQ ID NO:1) and 400 nM Strand B (5'-ACAAACATGA-BHQ1-3') (SEQ ID NO:2) were added to a 100 mM $NaNO_3$ and 10 mM MOPS (3-(N-morpholino)propanesulfonic acid) pH 7.2 buffer solution. The resulting solution was kept at room temperature for 1 hr to hybridize the two strands. Then 500 µL of the sensor solution prepared above were transferred to a cuvette. The cuvette was placed in a fluorimeter (Fluoro-Max-P; Horiba JobinYvon, Edison, N.J.) at 25° C. The excitation frequenct was set at 491 nm and the emission at 518 nm was monitored. After an initial reading, the cuvette was taken out, and a small volume of concentrated $Hg^{2+}$ solution was added. After vortexing, the cuvette was returned into the fluorimeter to continue the kinetic measurements.

```
Alternative polynucleotides that could be used
include Strand C
                                       (SEQ ID NO: 3)
(5'-FAM-TCATGTTTCTTCTGTTGCCCCCTTCTGTTGTAT-3'), Strand D
                                       (SEQ ID NO: 4)
(5'-FAM-TCATGTTTCTTCTGTTGCCCCCTTCTGTTGTTT-3'),
and Strand E
                                       (SEQ ID NO: 5)
(5'-FAM-TCATGTTTCTTCTGTTGGGGGCTTCTGTTGTTT-3').
```

Selectivity Assay

To determine the selectivity of the sensor, 1 µM of each of a number of metal ions, including $Mg^{2+}$, $Ca^{2+}$, $Mn^{2+}$, $Co^{2+}$, $Ni^{2+}$, $Cu^{2+}$, $Pb^{2+}$, $Zn^{2+}$, $Cd^{2+}$, and $Hg^{2+}$, was added to the sensor solution, and the fluorescence increase induced by each metal ion was monitored with a fluorimeter. In addition, 1 µM $Hg^{2+}$ and 1 µM of another metal ion were added together to the sensor solution and the fluorescence change was recorded. This assay was carried out for each of the metal ions.

Mercury Detection in Pond Water

A pond water sample was collected from the University of Illinois campus and filtered through a 0.22 µm membrane prior to testing. 180 µL of the pond water was then mixed with a concentrated buffer and a $Hg^{2+}$ solution to reach a final volume of 200 µL of a first mixture containing 500 nM $Hg^{2+}$, 100 mM $NaNO_3$ and 10 mM MOPS at pH 7.2. 300 µL of a concentrated sensor solution was then mixed with 200 µL of the first mixture, obtaining a final mixture containing 200 nM $Hg^{2+}$ and 100 nM hybridized DNA. The fluorescence of the final mixture was monitored with a fluorimeter.

REFERENCES

1. O. I. Joensuu, *Science* 1971, 172, 1027.
2. O. Malm, *Environ. Res.* 1998, 77, 73.
3. P. B. Tchounwou, W. K. Ayensu, N. Ninashvili and D. Sutton, *Environ. Toxicol.* 2003, 18, 149.
4. L. Prodi, C. Bargossi, M. Montalti, N. Zaccheroni, N. Su, J. S. Bradshaw, R. M. Izatt and P. B. Savage, *J. Am. Chem. Soc.* 2000, 122, 6769.
5. X. Guo, X. Qian and L. Jia, *J. Am. Chem. Soc.* 2004, 126, 2272.
6. A. Caballero, R. Martinez, V. Lloveras, I. Ratera, J. Vidal-Gancedo, K. Wurst, A. Tarraga, P. Molina and J. Veciana, *J. Am. Chem. Soc.* 2005, 127, 15666.

7. Y. K. Yang, K. J. Yook and J. Tae, *J. Am. Chem. Soc.* 2005, 127, 16760.
8. S. H. Kim, J. S. Kim, S. M. Park and S.-K. Chang, *Org. Lett.* 2006, 8, 371.
9. M. H. Ha-Thi, M. Penhoat, V. Michelet and I. Leray, *Org. Lett.* 2007, 9, 1133.
10. E. M. Nolan and S. J. Lippard, *J. Am. Chem. Soc.* 2007, 129, 5910.
11. S. Yoon, E. W. Miller, Q. He, P. H. Do and C. J. Chang, *Angew Chem. Int. Ed.* 2007, 46, 6658.
12. X. F. Liu, Y. L. Tang, L. H. Wang, J. Zhang, S. P. Song, C. Fan and S. Wang, *Adv. Mater.* 2007, 19, 1471.
13. Y. Zhao and Z. Zhong, *Org. Lett.* 2006, 8, 4715.
14. Y. Zhao and Z. Zhong, *J. Am. Chem. Soc.* 2006, 128, 9988.
15. M. Virta, J. Lampinen and M. Karp, *Anal. Chem.* 1995, 67, 667.
16. P. Chen and C. He, *J. Am. Chem. Soc.* 2004, 126, 728.
17. M. Matsushita, M. M. Meijler, P. Wirsching, R. A. Lerner and K. D. Janda, *Org. Lett.* 2005, 7, 4943.
18. S. V. Wegner, A. Okesli, P. Chen and C. He, *J. Am. Chem. Soc* 2007, 129, 3474
19. A. Ono and H. Togashi, *Angew. Chem. Int. Ed.* 2004, 43, 4300.
20. C. K. Chiang, C. C. Huang, C. W. Liu and H. T. Chang, *Anal. Chem.* 2008, 80, 3716.
21. Y. Yamini, N. Alizadeh and M. Shamsipur, *Anal. Chim. Acta* 1997, 355, 69.
22. W. H. Chan, R. H. Yang and K. M. Wang, *Anal. Chim. Acta* 2001, 444, 261.
23. A. Widmann and C. M. G. van den Berg, *Electroanalysis* 2005, 17, 825.
24. V. Ostatna and E. Palecek, *Langmuir* 2006, 22, 6481.
25. J. S. Lee, M. S. Han and C. A. Mirkin, *Angew. Chem. Int. Ed.* 2007, 46, 4093.
26. G. K. Darbha, A. Ray and P. C. Ray, *Acs Nano* 2007, 1, 208.
27. D. Li, A. Wieckowska and I. Willner, *Angew. Chem. Int. Ed.* 2008, 47, 3927.
28. C. W. Liu, Y. T. Hsieh, C. C. Huang, Z. H. Lin and H. T. Chang, *Chem. Commun.* 2008, 2242.
29. X. J. Xue, F. Wang and X. G. Liu, *J. Am. Chem. Soc.* 2008, 130, 3244.
30. L. H. Wang, J. Zhang, X. Wang, Q. Huang, D. Pan, S. P. Song and C. H. Fan, *Gold Bull.* 2008, 41, 37.
31. Y. Miyake, H. Togashi, M. Tashiro, H. Yamaguchi, S. Oda, M. Kudo, Y. Tanaka, Y. Kondo, R. Sawa, T. Fujimoto, T. Machinami and A. Ono, *J. Am. Chem. Soc.* 2006, 128, 2172.
32. J. Liu and Y. Lu, *Angew. Chem. Int. Ed.* 2007, 46, 7587.
33. S. D. Jhaveri, R. Kirby, R. Conrad, E. J. Maglott, M. Bowser, R. T. Kennedy, G. Glick and A. D. Ellington, *J. Am. Chem. Soc.* 2000, 122, 2469.
34. R. Nutiu and Y. Li, *J. Am. Chem. Soc.* 2003, 125, 4771.
35. R. Nutiu and Y. Li, *Chem.-Eur. J.* 2004, 10, 1868.
36. M. N. Stojanovic, P. de Prada and D. W. Landry, *J. Am. Chem. Soc.* 2001, 123, 4928.
37. N. Hamaguchi, A. Ellington and M. Stanton, *Anal. Biochem.* 2001, 294, 126.
38. C. J. Yang, S. Jockusch, M. Vicens, N. J. Turro and W. H. Tan, *Proc. Natl. Acad. Sci. U.S.A.* 2005, 102, 17278.
39. Lakowicz, J. R. In Principles of Fluorescence Spectroscopy; 2nd ed.; Kluwer Academic/Plenum: New York, 1999.

What is claimed is:

1. A sensor for detecting mercury, comprising:
a first polynucleotide, comprising a first region, and a second region,
a second polynucleotide,
a third polynucleotide,
a fluorophore, and
a quencher,
wherein the third polynucleotide is optionally linked to the second region;
the fluorophore is linked to the first polynucleotide and the quencher is linked to the second polynucleotide, or the fluorophore is linked to the second polynucleotide and the quencher is linked to the first polynucleotide;
when the first region and the second region hybridize to the second polynucleotide, the quencher quenches the fluorophore; and
the second region binds to the third polynucleotide when in the presence of $Hg^{2+}$ ions, releasing the second polynucleotide so that the quencher does not quench the fluorophore.

2. The sensor of claim 1, wherein the fluorophore is linked to the 5' end of the first polynucleotide.

3. The sensor of claim 1, wherein the quencher is linked to the 3' end of the second polynucleotide.

4. The sensor of claim 1, wherein the fluorophore is linked to the 3' end of the second polynucleotide.

5. The sensor of claim 1, wherein the quencher is linked to the 5' end of the first polynucleotide.

6. The sensor of claim 1, wherein the fluorophore is FAM.

7. The sensor of claim 1, wherein the quencher is non-flourescent quenchers.

8. The sensor of claim 1, wherein the first polynucleotide comprises the nucleic-acid sequence of SEQ ID NO:1.

9. The sensor of claim 1, wherein the second polynucleotide comprises the nucleic acid sequence of SEQ ID NO:2.

10. The sensor of claim 1, wherein the the second region and the third polynucleotide form 2 to 20 thymine-thymine mismatches.

11. The sensor of claim 1, wherein the second region and the third polynucleotide form 4 to 10 thymine-thymine mismatches.

12. The sensor of claim 1, wherein the second region and the third polynucleotide form 5 to 8 thymine-thymine mismatches.

13. A method of detecting the presence of mercury in a sample, comprising:
(a) forming a mixture comprising the sample and a sensor comprising:
a first polynucleotide, comprising a first region, and a second region,
a second polynucleotide,
a third polynucleotide,
a fluorophore, and
a quencher,
wherein the third polynucleotide is optionally linked to the second region;
the fluorophore is linked to the first polynucleotide and the quencher is linked to the second polynucleotide, or the fluorophore is linked to the second polynucleotide and the quencher is linked to the first polynucleotide;
when the first region and the second region hybridize to the second polynucleotide, the quencher quenches the fluorophore; and
the second region binds to the third polynucleotide when in the presence of $Hg^{2+}$ ions, releasing the second polynucleotide so that the quencher does not quench the fluorophore, and
(b) measuring the fluorescence of the mixture.

14. The method of claim 13, wherein the fluorophore is linked to the 5' end of the first polynucleotide.

15. The method of claim 13, wherein the quencher is linked to the 3' end of the second polynucleotide.

16. The method of claim 13, wherein the fluorophore is linked to the 3' end of the second polynucleotide.

17. The method of claim 13, wherein the quencher is linked to the 5' end of the first polynucleotide.

18. The method of claim 13, wherein the fluorophore is FAM.

19. The method of claim 13, wherein the quencher is non-flourescent quenchers.

20. The method of claim 13, wherein the second region and the third polynucleotide form 4 to 10 thymine-thymine mismatches.

21. The method of claim 13, wherein the sample comprises a water sample.

22. The method of claim 13, wherein the sample comprises a bodily fluid.

23. The method of claim 13, wherein an increase in fluorescence is indicative of the presence of mercury.

24. A method of determining the concentration of mercury in a sample, comprising:
   (a) forming a mixture comprising the sample and a sensor comprising:
   a first polynucleotide, comprising a first region, and a second region,
   a second polynucleotide,
   a third polynucleotide,
   a fluorophore, and
   a quencher,
   wherein the third polynucleotide is optionally linked to the second region;
   the fluorophore is linked to the first polynucleotide and the quencher is linked to the second polynucleotide, or the fluorophore is linked to the second polynucleotide and the quencher is linked to the first polynucleotide;
   when the first region and the second region hybridize to the second polynucleotide, the quencher quenches the fluorophore; and
   the second region binds to the third polynucleotide when in the presence of $Hg^{2+}$ ions, releasing the second polynucleotide so that the quencher does not quench the fluorophore,
   (b) measuring the fluorescence of the mixture; and
   (c) comparing the measurement obtained in (b) with that of a calibration curve created using known concentrations of mercury.

25. The method of claim 24, wherein the second region and the third polynucleotide form 4 to 10 thymine-thymine mismatches.

26. The method of claim 24, wherein the sample comprises a water sample.

27. The method of claim 24, wherein the sample comprises a bodily fluid.

\* \* \* \* \*